(12) United States Patent
Rosen et al.

(10) Patent No.: US 9,492,139 B2
(45) Date of Patent: Nov. 15, 2016

(54) NON-IMAGING LOW FREQUENCY ULTRASONIC TESTING AND DIAGNOSTIC EVALUATION SYSTEM

(75) Inventors: Yitzhak Rosen, Washington, DC (US); B. Boro Djordjevic, Serverna Park, MD (US)

(73) Assignee: ULTRASONIC MEDICAL MAPPING, LLC, Glen Burnie, MD (US)

( * ) Notice: Subject to any disclaimer, the term of this patent is extended or adjusted under 35 U.S.C. 154(b) by 70 days.

(21) Appl. No.: 13/979,605

(22) PCT Filed: Jan. 13, 2012

(86) PCT No.: PCT/US2012/021308
§ 371 (c)(1),
(2), (4) Date: Aug. 9, 2013

(87) PCT Pub. No.: WO2012/097294
PCT Pub. Date: Jul. 19, 2012

(65) Prior Publication Data
US 2013/0310688 A1      Nov. 21, 2013

Related U.S. Application Data

(60) Provisional application No. 61/432,454, filed on Jan. 13, 2011.

(51) Int. Cl.
*A61B 8/00* (2006.01)
*A61B 8/08* (2006.01)

(52) U.S. Cl.
CPC . *A61B 8/00* (2013.01); *A61B 8/08* (2013.01); *A61B 8/4483* (2013.01)

(58) Field of Classification Search
CPC ......... A61B 8/00; A61B 8/08; A61B 8/4483
See application file for complete search history.

(56) References Cited

U.S. PATENT DOCUMENTS

| | | |
|---|---|---|
| 4,941,474 A | 7/1990 | Pratt |
| 5,921,929 A | 7/1999 | Goll et al. |
| 7,344,509 B2 | 3/2008 | Hynynen et al. |
| 2005/0004457 A1 | 1/2005 | Moilanen et al. |
| 2007/0014480 A1* | 1/2007 | Sirohey et al. ............... 382/240 |
| 2007/0044559 A1 | 3/2007 | Andrews |
| 2007/0293906 A1 | 12/2007 | Cowan et al. |
| 2008/0114239 A1 | 5/2008 | Randall et al. |

(Continued)

OTHER PUBLICATIONS

International Search Report/Written Opinion mailed May 10, 2012 for International Application No. PCT/US2012/021308.

*Primary Examiner* — Jonathan Cwern
(74) *Attorney, Agent, or Firm* — Seyfarth Shaw LLP

(57) ABSTRACT

Disclosed are non-imaging low frequency ultrasound apparatus and methods that extend the range of ultrasonic applications to medical testing and diagnostics. More particularly, apparatus and methods for generating, transmitting and receiving low frequency ultrasound through a test body can be used to generate non-imaging medical mapping of ultrasound signals and medical diagnostics. Typically frequencies below 1 MHz are generated by a low frequency non-imaging wide aperture transmitting transducer and received by multiple low frequency small aperture receiving transducers and processed via improved signal processing to evaluate and map the ultrasound interactions for detecting and characterizing clinical conditions in test objects.

29 Claims, 14 Drawing Sheets

(56) References Cited

U.S. PATENT DOCUMENTS

| | | |
|---|---|---|
| 2008/0242995 A1 | 10/2008 | Lee et al. |
| 2009/0089025 A1 | 4/2009 | Doyle |
| 2009/0149748 A1 | 6/2009 | Lenhardt et al. |
| 2009/0247869 A1 | 10/2009 | Rambod et al. |

\* cited by examiner

Ultrasonic: Contact, Remote and Scanning
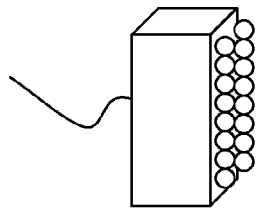
Transducer Arrays
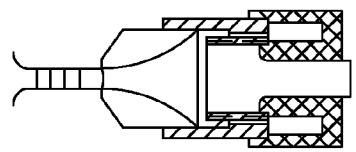
Water-Jet
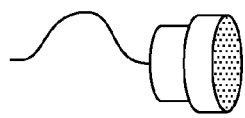
Contact
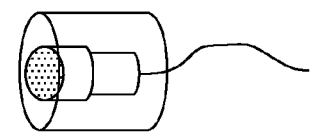
Water-Bubbler
EMAT
Conventional types of ultrasonic transducers that can be applied in testing
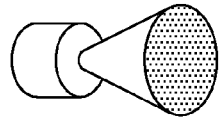
Gas (air) Coupled
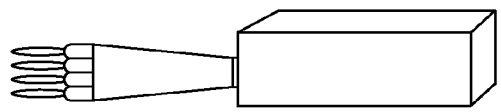
Laser Generator
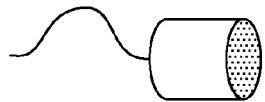
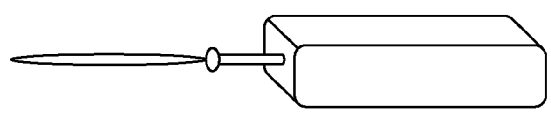
Laser Receiver
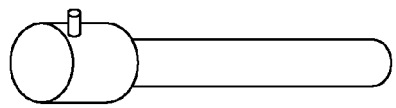
Waveguide Coupled
Advanced types of ultrasonic transducers that can be applied in testing
FIG. 6

FIG. 8. Ultrasonic signal acquisition path for lower frequency ultrasonic clinical testing. The above steps can be augmented via signal processing and signal gating methods.

NON-IMAGING LOW FREQUENCY ULTRASONIC TESTING AND DIAGNOSTIC EVALUATION SYSTEM

CROSS-REFERENCE TO RELATED APPLICATIONS

This application is a national phase filing under 35 U.S.C. §371 of International Patent Application No. PCT/US2012/021308 filed Jan. 13, 2012 which claims priority to U.S. Provisional Patent Application No. 61/432,454 filed Jan. 13, 2011 in the name of Rosen et al. entitled NON-IMAGING LOW FREQUENCY ULTRASONIC TESTING AND DIAGNOSTIC EVALUATION SYSTEM, each of which is hereby incorporated by reference in its entirety.

TECHNICAL FIELD

The disclosure herein relates to low frequency ultrasonic testing and diagnostic systems and methods. More particularly, the disclosure herein relates to such systems and methods employing low frequency ultrasound mapping for medical testing and diagnosis. This disclosure is directed to non-imaging low frequency ultrasonic systems and methods.

BACKGROUND

Ultrasonic wave propagation, signal attenuation and signal interface loss in the human body are a function of frequency. For imaging ultrasound, the sound wave frequency must be higher than that of a sufficiently short wavelength to enable imaging resolution of the scattered and reflected signals. This requirement limits testing in the human body to areas that can be penetrated by higher frequency ultrasonic signals usually above 1 MHz. Among other things, there is a need to extend the range of ultrasonic applications to medical diagnostics that will not be limited by imaging wavelengths resolution requirements.

Ultrasonic measurements can be performed in a range of methods and applications. In medicine, major effort is placed in ultrasonic imaging where ultrasonic echoes are analyzed forming 1D, 2D or even 3D images of the target signal reflections. The ultrasonic test frequencies for imaging are in general above 1 MHz with an upper range of 20 MHz or more. Volume test coverage is achieved with ultrasonic transducer movement or the wobble of the transducer axis ultrasonic beam. Most modern imaging instruments use array transducers and employ phase array ultrasonic signal processing. With very few notable exceptions, transducers or phase arrays are driven by controlled shape electrical impulses. Ultrasonic signal reflections, time gating and image formation in medical high-frequency ultrasound explores extensive signal processing algorithms including distance amplitude correction, frequency filtering, Doppler signal extraction, signal threshold corrections, noise reduction correlation methods and more.

In therapeutic ultrasonic applications, as opposed to diagnostic applications, ultrasonic signal frequencies are often below 1 MHz and the transducers emit range of sound intensities and signal waveforms including r.f. type signals and customized impulses (r.f. or r.f. signal as used herein means a multi-cycle ultrasonic signal with certain duration and frequency content). None of these applications are usable for the diagnostic ultrasonic measurements.

Except for a possible few notable exceptions, ultrasonic diagnostic equipment has a mono-static (pulse echo) configuration where transmitter and receiver transducers are collinear in the test space. Bi-static diagnostic measurement configurations have not been considered and there is no practical ultrasonic equipment that uses physically separated transmitter and receiver transducers. Bi-static configurations are extensively used in the ultrasonic nondestructive testing technologies where through transmission (opposing transmitter and receiver transducer set) is commonly used in ultrasonic test configurations.

In conventional ultrasonic imaging applications, all transducers are coupled and in contact with the test object. Using contact transducers in mono-static geometry, above 1 MHz has enabled the development of a broad array of useful ultrasonic test configurations capable of imaging internal organs, fetus and other medically interesting targets.

Acoustical and ultrasonic waves at lower frequencies, e.g. 25 kHz to 1 MHz are used in other applications including seismology, underwater acoustics and nondestructive materials testing. At these lower frequencies more recent developments of non-contact air coupled transducers make possible ultrasonic testing without the need to contact the test object.

As always, there is a need for new, different, and/or improved methods of testing and diagnostics in the medical profession. Accordingly, employing ultrasound at relatively low frequency domains (e.g. 25 kHz to 1 MHz) and low power levels in a testing or diagnostic fashion fills a need in the art, as does the development of apparatus, systems, and methodologies to facilitate such use. Applicants have invented such apparatus, systems and methods employing low frequency ultrasound as a non-imaging test and/or diagnostic.

SUMMARY

Some embodiments provide a method employing low frequency ultrasonics for medical diagnosis, the method comprising propagating low frequency ultrasonic signals in to a test object using one or more transmitting transducers, each transmitting transducer comprising an aperture, each transmitting transducer aperture comprising a multiple of an acoustical wavelength of each low frequency ultrasonic signal, wherein the low frequency is a frequency below about 1 MHz, wherein each of the propagated low frequency ultrasonic signals is affected and modified by internal features of the test object; receiving the propagated low frequency ultrasonic signals passed through the test object using one or more receiving transducers, each receiving transducer comprising a plurality of apertures, each receiving transducer aperture comprising a fraction of the acoustical wavelength of each low frequency ultrasonic signal, wherein the received low frequency ultrasonic signals comprises modifications of the propagated low frequency ultrasonic signal representing the internal features of the test object; processing the received low frequency ultrasonic signals to extract clinically significant changes in the received ultrasonic signals; and correlating, using a processor, the processed signals to medically significant features of the test object for medical diagnosis.

In some embodiments, the processing of the received low frequency ultrasonic signals further comprises conditioning the signals by one or more amplifiers and one or more analog signal conditioning filters.

In some embodiments, a controlled bandwidth of the one or more amplifiers and one or more analog signal conditioning filters is in the range of about 20 KHz to about 1 MHz.

In some embodiments, the processing of the received low frequency ultrasonic signals further comprises digitizing the received signals by converting analog data to digital format.

In some embodiments, the correlating further comprises mapping the processed signals to clinically significant information relating to the test object.

In some embodiments, the presence of a medical condition is extracted from a comparison of observed changes in the received low frequency ultrasonic signals to historical data.

In some embodiments, the processed signals comprise a plurality of data points relating to the test object, wherein grouping of data points is indicative of a possible target of medical significance and position within the test object, wherein the method further comprises mapping the plurality of data points in a graphical representation to help with medical diagnosis.

In some embodiments, the signal processing further comprise signal gating and segmenting determined by dynamic signal processing.

In some embodiments, the received low frequency ultrasonic signals are captured as r.f. signals and envelope signals suitable for digital signal processing, wherein the signal processing further comprises processing data records of the r.f. signals to define clinically significant portions of the data; processing the envelope signals to define clinically relevant signatures; time segmenting the r.f. signals to components determined by envelope analysis; analyzing the r.f. signals for clinically significant features; and fusing data from the r.f. signals and the envelope signals processing and performing statistical analysis using historical data and clinically significant ultrasonic feature markers to predict clinical diagnosis.

In some embodiments, the statistical analysis is a Bayesian statistical analysis.

Some embodiments provide a non-imaging low frequency ultrasonic evaluation system, the system comprising a transmitting transducer for transmitting a wavefront of a test wavelength, wherein the transmitting transducer comprises an aperture that has a width that is a multiple of the test wavelength; a receiving transducer wherein the receiving transducer comprises an aperture that has a width that is a fraction of the test wavelength, analog processing wherein signals are captured with large dynamic amplitude range; and a microprocessor adapted to receive, store and display data obtained via the receiving transducer.

In some embodiments, the transmitting transducer and the receiving transducer are independently selected from no contact air-coupled transducers, water jet transducers, contact transducers, immersion piezoelectric transducers, and combinations thereof.

In some embodiments, the transmitting transducer and the receiving transducer are of different types.

In some embodiments, the transmitting transducer aperture has a width of about 2 to about 10 times the test wavelength.

In some embodiments, the transmitting transducer aperture has a width of about 5 times the test wavelength.

In some embodiments, the transmitting transducer is adapted to project r.f. gated impulse low frequency ultrasonic waveforms.

In some embodiments, the receiving transducer comprises an aperture that has a width that is less than about 30% of the test wavelength.

In some embodiments, the receiving transducer comprises a plurality of receiving transducers.

In some embodiments, the receiving transducer is configured as a bi-static system.

In some embodiments, the receiving transducer is configured as a mono-static system.

Some embodiments provide a method of evaluating a test object via non-imaging low frequency ultrasound, the method comprising providing a test object; projecting a low frequency ultrasonic wavefront into the test object; receiving ultrasonic signals that have been modified from the projected wavefront by one or more of the test objects and significant feature thereof that cause one or more of frequency change, ultrasonic wavefront distortion, signal attenuation, signal scattering, or other change to the projected ultrasonic wavefront; performing data analysis on the received modified ultrasonic signals; and mapping the signals as a graphical representation of the data.

In some embodiments, the projected ultrasonic wavefront is planar.

In some embodiments, the projected low frequency ultrasonic wavefront has a frequency of less than 1 MHz.

In some embodiments, the projected low frequency ultrasonic wavefront has a frequency of about 20 kHz to about 1 MHz.

In some embodiments, the projected low frequency ultrasonic wavefront is a single frequency about two to five wavelengths which is generated normal to a transmitting transducer generating the wavefront.

In some embodiments, the projected ultrasonic wavefront comprises r.f. gated impulses.

In some embodiments, the r.f. gated impulses comprise two or more low frequency wavelengths.

In some embodiments, the projected ultrasonic wavefront is a non-focused wavefront.

In some embodiments, the wavefront is generated by a transmitting transducer comprising an aperture that has a width that is a multiple of the test wavelength.

In some embodiments, the ultrasonic signals are received by one or more receiving transducers comprising an aperture that has a width that is a fraction of the test wavelength.

In some embodiments, the one or more receiving transducers are selected from mono-static or bi-static configurations.

In some embodiments, the test object is selected from a living organism, a dead organism, living tissue, non-living tissue, functioning tissue, malfunctioning tissue, or non-functioning tissue, and combinations thereof.

In some embodiments, the test object is a human body part selected from the head, the chest cavity, and the breast.

In some embodiments, the test object is a human body system.

The embodiments disclosed herein are meant to be illustrative in nature only. Additional embodiments that fall within the scope and spirit of this disclosure are intended to be captured by this disclosure as well.

BRIEF DESCRIPTION OF THE DRAWINGS

The drawings submitted herewith show some embodiments or features of some embodiments encompassed by the disclosure. The drawings are meant to be illustrative and are not intended to be limiting. Like reference numeral refer to like elements through the drawings.

FIG. 6 depicts various types of transducers which may be employed by various embodiments described herein;

DETAILED DESCRIPTION OF EXEMPLARY EMBODIMENTS

Figure 1:
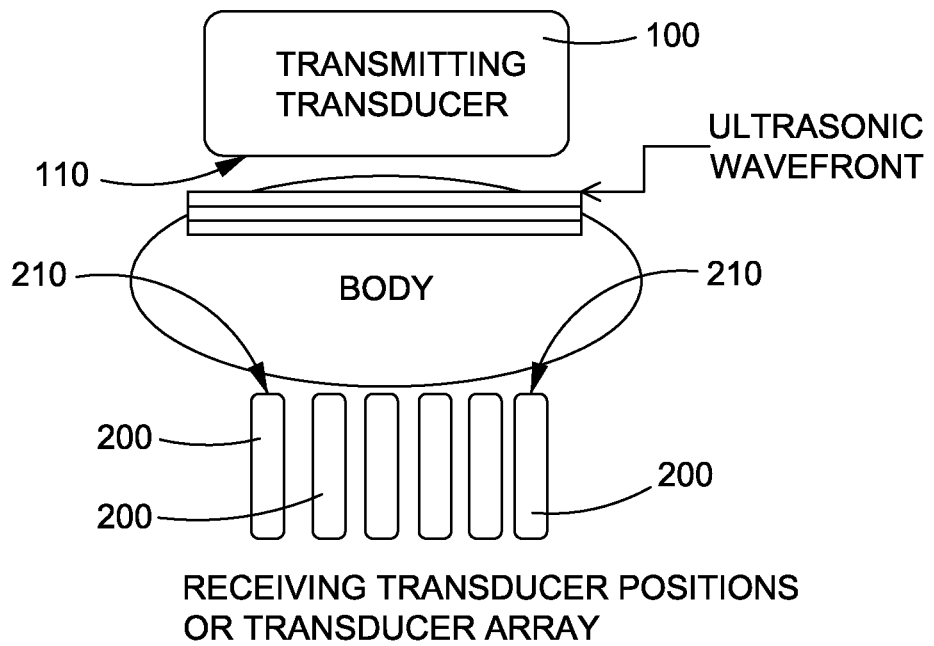
FIG. 1 is a schematic drawing of a bi-static ultrasound transducer setup suitable for use with some embodiments described herein.

Embodiments of the present invention extend the range of ultrasonic applications to medical diagnostics, in part because lower frequency ultrasonic signals can propagate over longer ranges and thus ultrasonic signals can retain the signatures from body feature(s) or system(s). In short, we are able to use the non-imaging modifications of the low frequency ultrasonic wave front features using signal-processing methods. The data yielded through this process can be analyzed and correlated to medically (clinically) significant features. Embodiments of the invention reflect this scientific methodology and represent a radical departure from current high frequency ultrasonic imaging and associated diagnostic practices.

Embodiments of the non-imaging low frequency ultrasonic testing and diagnostic evaluation system and methods provide testing and validating ultrasonic measurements using contact, water-jet and non-contact air-coupled transducers in the lower frequency domain—i.e., generally below 1 MHz. Non-imaging transmitting and receiving transducers can be large in diameter with transmitting transducers having many wavelengths aperture size while receiving transducers can be of sub-wavelength aperture sizes. By using lower frequencies and combinations of larger aperture transmitting transducers and smaller aperture receiving transducers, embodiments of the ultrasonic set ups are expected to improve the depth and range of the ultrasonic test thus mitigating problems often encountered in imaging applications. In summary, embodiments of the present invention will better enable more automated diagnostic testing while reducing the load on the manual interpretation of the measurements.

Embodiments of the present invention incorporate lower frequency ultrasonic signals (e.g., below about 1 MHz) (capable of propagating over longer ranges) and ultrasonic signals (capable of retaining the signatures from human body features) to extend the range of ultrasonic applications to medical diagnostics and diagnostics and ultrasonic medical mapping rather than ultrasonic imaging. In context of this descriptions "ultrasonic medical mapping" is defined as ultrasonic medical testing primary at sub-imaging wavelengths and frequencies using measurement and recording techniques which are not primarily designed to produce images, but which produce data viable to be represented as maps (i.e. containing localization and diagnostic information).

Embodiments of the present invention incorporate non-imaging modifications of the wave front features using signal-processing methods. The data yielded through this process may be analyzed and correlated to medically (clinically) significant features.

Embodiments of the present invention incorporate a methodology that records local variances of the ultrasound in clinical testing without the need to resolve the targets via reception of the backscattering ultrasonic signals.

Embodiments of the present invention incorporate the methodology that lower frequency ultrasonic test configurations enable broader access to high ultrasonic attenuation tissue. Even at non-imaging wavelengths, ultrasound body interactions can be mapped and used to both characterize and detect clinical conditions in body areas such as the lungs, kidneys, brain and others that are not accessible using high frequency imaging methods. By using lower transmitting frequencies and transmitting transducers having larger source apertures, the proposed ultrasonic apparatus test set ups are expected to improve the depth and range of the ultrasonic test thus mitigating problems often encountered in higher frequency imaging applications. The data collected, measured, and recorded from these sub-imaging wavelengths may be represented as maps containing localization and diagnostic information, i.e. medical mapping.

Embodiments of the present invention incorporate the use of ultrasonic measurements using immersion, contact, water jet coupled, and non-contact air-coupled transducers in the lower frequency domain. In some cases, laser ultrasonic via conversion layers between body and laser light may also be used.

Embodiments of the present invention capture how the low frequency ultrasonic signals propagating through the body are affected and modified by internal features of the body (e.g. body system or body systems, or part thereof, tissues, organs, bone, vessels, etc.) and how that can induce characteristic signal features to the ultrasonic waveforms.

Embodiments of the present invention analyze how these features can enable recognition of the normal versus clinically significant body changes and conditions to guide and help in medical diagnosis. There are many ultrasonic changes that can be effectively captured using the above described test configurations including variances in attributes of the test object such as, for example, body density, fluid flow (such as blood), size of the features (such as lungs, heart or bladder) and changes of conditions (such as presence of space occupying lesion (e.g. tumor) and/or foreign matter (e.g. projectile, coin, etc.). The presence of medical conditions can be extracted from the observed changes to normal responses and tracked via advanced signal processing algorithms such as Doppler sound shifts, resonances, or more sophisticated waveform classifier.

Traditionally, the use of lower ultrasonic frequency testing has been considered unsuitable for imaging because of the longer wavelengths of the probing ultrasonic wave. The transducer test configurations that are required also preclude simple pulse echo imaging configuration. However, lower ultrasonic frequencies signals have been demonstrated to propagate in the more complex tissue such as lungs, bone, across air gaps, and other tissues, while still being able to interact and be modified by the biological interfaces and tissue characteristics. The inventors have discovered that these lower ultrasonic frequencies are well-suited to non-imaging testing and diagnostics.

With the application of modern instrumentation, better analog to digital conversion, advancements in computing capabilities, advanced signal processing and modern ultrasonic transduction, it is possible to look at medical diagnostics needs via non-imaging ultrasonic methods that can interrogate low density tissue such as lungs, cross air gaps or interact with dense material such as bone. By capturing specific ultrasonic signal interaction signals retained from test object features (e.g. body feature(s) or body system(s)), one can diagnose medically meaningful physical conditions. This technology has significant potential towards automation and computer aided diagnostics. The low frequency ultrasonics can be explored for diagnostics of a variety of medical conditions such as, but not limited to, brain tissue abnormalities, lungs, small and large intestines, large or dense breast and other organs wherein tissue structure or air gaps create impedance barriers that prevent using current medical high frequency ultrasonic imaging tools.

Ultrasound has advantages over X-ray imaging which senses radiation attenuation as a function of body density. Ultrasonic waves are mechanical waves that can interact with microstructures, interfaces, geometries and can sense changes in the mechanical properties of the testing media (e.g. body system(s)). It must be noted that ultrasound does not involve ionizing radiation and, at low intensity levels, is not harmful to the living cell tissue.

The low frequency approach described herein requires radical departure from conventional thinking in high-frequency ultrasonic imaging procedures and requires development of new methodology, test equipment, test analysis and clinical interpretation tools.

The non-imaging low frequency ultrasonic testing and diagnostic evaluation system disclosed herein uses a methodology to record local variances of the ultrasound in clinical testing without the need to image acoustical fields or resolve the targets via reception of the backscattering ultrasonic signals. Lower frequency ultrasonic test configurations enable broader access to high ultrasonic attenuation tissue. Low frequency ultrasonic waves are essentially wavelengths that are too long for back scattering imaging. In general, below about 1 MHz to about 50 kHz, these signals more readily propagate across gas gaps, and in complex human anatomical features such as head, chest cavity or abdominal region. Low frequency ultrasonic signals can propagate in bones and gas rich organs. In other embodiments, frequencies down to about 20 kHz may be used. Thus, the low frequency ultrasound referred to herein generally means frequencies below about 1 MHz, and typically from about 20 kHz to less than about 1 MHz. Some embodiments may use low frequencies such as 10 kHz, 20 kHz, 30 kHz, 40 kHz, 50 kHz, 60 kHz, 70 kHz, 80 kHz, 90 kHz, 100 kHz, 150 kHz, 200 kHz, 250 kHz, 300 kHz, 350 kHz, 400 kHz, 450 kHz, 500 kHz, 550 kHz, 600 kHz, 650 kHz, 700 kHz, 750 kHz, 800 kHz, 850 kHz, 900 kHz, 950 kHz, 975 kHz, and 1 MHz and ranges between any two of these.

Ultrasonic signals propagating through the body are affected and modified by internal features of the test object, e.g. body organs and systems that can induce characteristic signal signatures to the ultrasonic waveforms. Analysis of these characteristic signal features can enable recognitions of the normal versus clinically significant variances in attributes of the test object, such as but not limited to body changes and conditions to guide and help in medical diagnosis. There are many ultrasonic changes that can be effectively captured using the test configurations described herein including variances in attributes such as body density, fluid flow such as blood, size of the features such as lungs, heart or bladder and changes of organ conditions such as presence of space occupying lesion (e.g. tumor) and/or foreign matter (e.g. projectile, coin, etc.). The presence of a medical condition can be extracted from the observed changes to normal responses and tracked via advanced signal processing algorithms such as Doppler sound shifts, resonances, or more sophisticated waveform classifier features now used for acoustics, sonar or radar applications.

In materials testing applications such as ultrasonic C-scan testing of composites, very detailed ultrasonic materials sensing can be achieved via test configurations that map ultrasonic signal changes such as attenuation or change other ultrasonic waveform signal features but do not image the ultrasonic signals. These measurements can be done at long ultrasonic wavelengths that cannot spatially resolve individual sound scattering locations. Even at non-imaging wavelengths, ultrasound body interactions can be mapped and used to both characterize and detect clinical conditions in body areas such as lung, kidney, brain and other body areas or systems, that are not accessible using high frequency imaging methods, such low frequency, non-imaging wavelengths may be referred to as "mapping wavelengths". The apparatus and methods disclosed herein have broad applicability across a myriad of functional areas and can be used for early detection of tissue abnormalities, masses, and any other anomaly. Mapping wavelengths can be generally defined as ultrasonic signals wavelengths that are modified by test media interactions but are too long to use ultrasonic imaging procedures.

With reference to the drawing figures, we now describe some embodiments of the low frequency non-imaging ultrasound diagnostic system and methods.

As used herein, "mapping" or "medical mapping" includes graphic presentation of processed ultrasonic signals for diagnostic use. Presentation can be multidimensional or a layered, coded compilation of the test data results including interactive operator access to clinically significant information including, but not limited to localization and diagnostic information.

r.f. or r.f. signal as used herein means a multi-cycle ultrasonic signal with certain duration and frequency content r.f. impulse (pulsed r.f.) as used herein means multi-cycle signal with defined number of cycles, defined envelope and phase. Signals can be narrow in frequency or intentionally modified such as in chirp signal up-chirp or down-chirp mode.

As shown in FIG. 1, some embodiments provide a bistatic, through transmission arrangement incorporating transmitting and receiving transducers. The transmitting transducer 100 has a large aperture (represented in the drawing by the size of box 100). The transmitting transducer 100 may be controlled by, for example, transducer size which is often many wavelengths in width across the transmitting face 110. This enables generation of planar lower frequency acoustical source. Receiving transducers 200 can be of significantly smaller aperture, for example, often with receiving surface 210 size of only a fraction of the acoustical wavelength. This transducer arrangement improves spatial discrimination of the received acoustical wavefront. Transducers aperture size is determined by test frequency and by desired resolution of the ultrasonic wave-front signal. Typical receiving transducers effective aperture sizes are less than 30% while transmitting transducers apertures supporting well formed planar wave-fronts need to have apertures size of over 5 times the acoustical wavelength. The angular orientation of the receiving transducers 200 can also be adapted to the best receiving conditions. Because sound can be diffracted, refracted and scattered from the body features, the receiving transducers 200 may be pre-positioned at anticipated body-signal redirection angles. Thus, a receiving transducer's axis may be at an angle with respect to the transmitting transducer axis. In a body examination test, the receiving transducer(s) can be angularly scanned to measure specific sound path deviations caused by the body. Through transmission ultrasonic signals can be collected via transducer array, scanned in plane via transducer, or captured via more complex spatial scan plan as dictated by the test needs.

Figure 2:
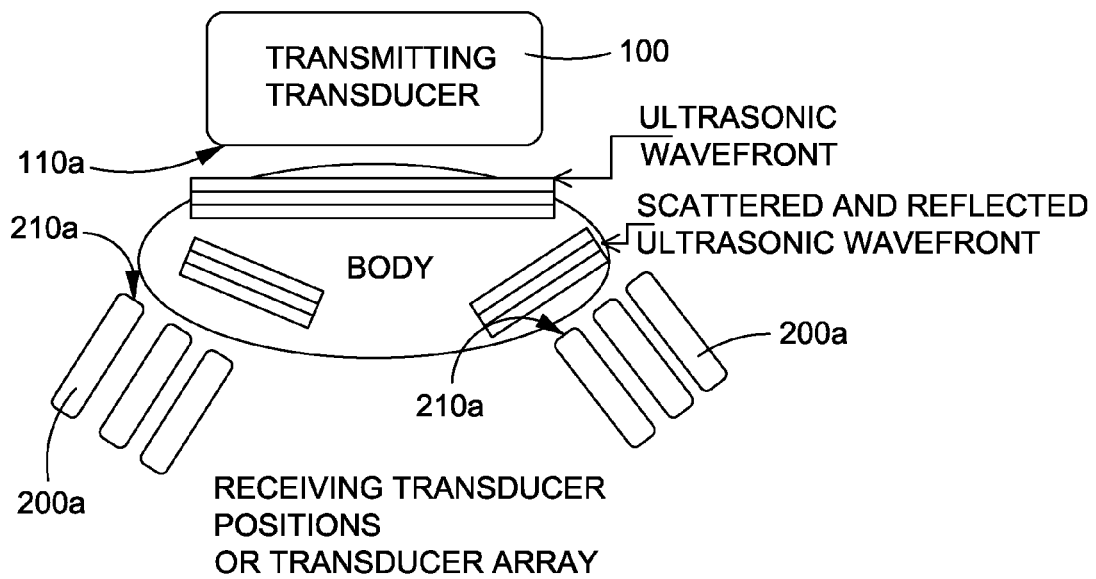
FIG. 2 is a schematic drawing of a bi-static ultrasound transducer setup with angularly displaced receiving transducers suitable for use with some embodiments described herein.

FIG. 2 shows a transmitting transducer 100 and receiving transducers 200 arranged in an angular displacement to account for anticipated body signal redirection angles. Any of a number of such angles can be employed. Multiple receiving transducers 200 may be employed to cover several angles at once, or they may be moved and rearranged over several testing sessions to achieve a complete data set.

Figure 3:
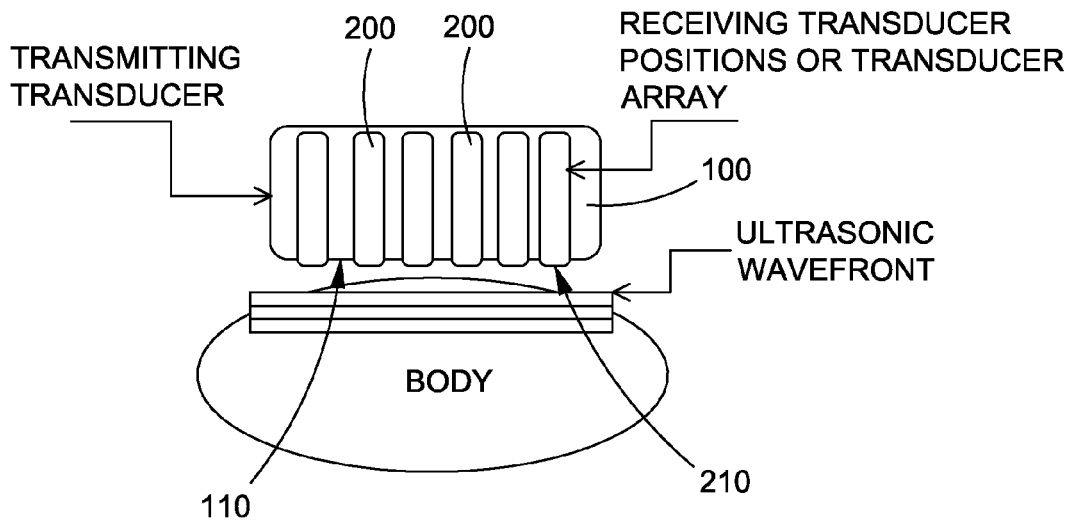
FIG. 3 is a schematic drawing of a mono-static ultrasound transducer setup suitable for use with some embodiments described herein.

As shown in FIG. 3, some embodiments provide a mono-static, pulse echo or back scattering ultrasonic data collection configuration. The transmitting and receiving sensors (100 and 200, respectively) functions' can be shared, or, for optimized power generation (and receiver sensitivity), the transmitting and receiving transducers can be separated in a spatially appropriate hybrid configuration. As described with reference to FIG. 1, the acoustical signal field can be examined via scanning motions or via transducer array configurations. Special test conditions (such as acquisition of a Doppler signal) might require angulations of the transducers.

FIG. 1 through FIG. 3 illustrate possible bi-static and mono-static transducer configurations that enable low frequency non-imaging testing of the human body. Transducer arrays, moving transducer configurations and sparse/partial transducer configurations can be implemented to transmit or receive ultrasonic signal. Ultrasonic signal can be analog processed via custom amplifiers and/or filters and digitized for advanced signal processing. Signal reconstruction via algorithms can be performed to create spatial and time domain information that correlates to important medical features. Ultrasonic transmission can be via traditional piezoelectric based transduction devices or advanced transduction such as laser ultrasonic means. Presentation of signal will be in the most favorable information format, including color graphic presentations of data depicting the human body structure with ultrasonic test information. Furthermore, ultrasonic data processing can be automated by means of available programmed data comparison algorithms and/or intelligent signal processing into simplified instructions or diagnostic statements.

The ultrasonic and acoustic phenomena is well described in literature as exemplified by books and references in the: P M Morse, K U Ingard, Theoretical Acoustics, Princeton University Press, 1968/1986; and K A Naugol'nykh, L A Ostrovsky, Nonlinear Acoustics, AIP Press 1994.

Also, there is technical information describing acoustic-ultrasonic signal processing exemplified by books and references such as: L J Ziomek, Fundamentals of Acoustic Field Theory and Space-Time Signal Processing, CRC Press, 1995; and C Heil, D E Walnut, Fundamental Papers in Wavelet Theory, Princeton University Press, 2006.

These complex analytical tools are only practical and valid, however, if the signal capture process and the fidelity of the ultrasonic signals is sufficient to enable meaningful signal processing. To date, low frequency ultrasound systems and measurements have not been developed for medical applications and have not been adapted for medical diagnostic purposes. In addition, T Kundu, Ultrasonic Non-destructive Evaluation, CRC Press, 2004 includes a summary of many advanced applications and potential clinical applications of ultrasonic tests. However, none of these works truly considers the benefits and applicability of lower frequency ultrasonic measurements, as disclosed in the present application and outlined in the following sections.

There are several fundamental issues that enable lower frequency ultrasonic testing. These factors are different than those required for imaging transducer testing which requires higher frequency and small aperture transducer configurations.

Source ultrasonic transducer is large in aperture, but can have planar or geometrically curved waveform-forming capability. The transducer output aperture size is relatively large, measuring from several to many acoustical wavelengths across the active transmission area. That is, the output aperture size is from about 2 to about hundred acoustical wavelengths in width, where the acoustical wavelength is dependent on the selected test frequency and test zone size. Typical transmitting aperture size dimensions is on the order of 5, to 10 wavelengths and can be square, rectangular or oblong in the shape. This relatively large aperture also enables generation of more power and better directional control. Signals, in general, are not an impulse, but are narrow band with specific r.f. features such as gated fixed frequency, chirped frequency content or are formed from more complex frequency components.

Receiving transducers may be of different size and apertures, but are in general much smaller than transmitting transducers and can be strategically positioned and oriented as discussed in the previous section. From 2 to hundreds receiving transducers may be employed. The transducers may be employed individually, or in groups of 2 or more receiving transducers. The receiving aperture is typically a fraction of the acoustical wavelength. The receiving aperture may be about 0.1 to about 0.9 times the width of the acoustical wavelength. The receiving aperture may be about 0.1, 0.2, 0.3, 0.4, 0.5, 0.6, 0.7, 0.8, 0.9 or a range between any two of these values times the acoustical wavelength in width. Receiving transducer(s) may be scanned or assembled as an array to capture features of the ultrasonic wave-fronts as they are modified by internal body features.

Transducer test geometry may be bi-static or mono-static. Mono-static configuration resembles conventional pulse echo geometry with the significant difference that transmitting and receiving transducers are not the same and are optimized for their ultrasonic functionality and modes of operation (as shown in FIG. 3). Bi-static configurations are in through transmission geometry (as shown in FIG. 1) as well as at other angular arrangements (as shown in FIG. 2). Combinations of these geometries may also be employed.

Figure 4A:
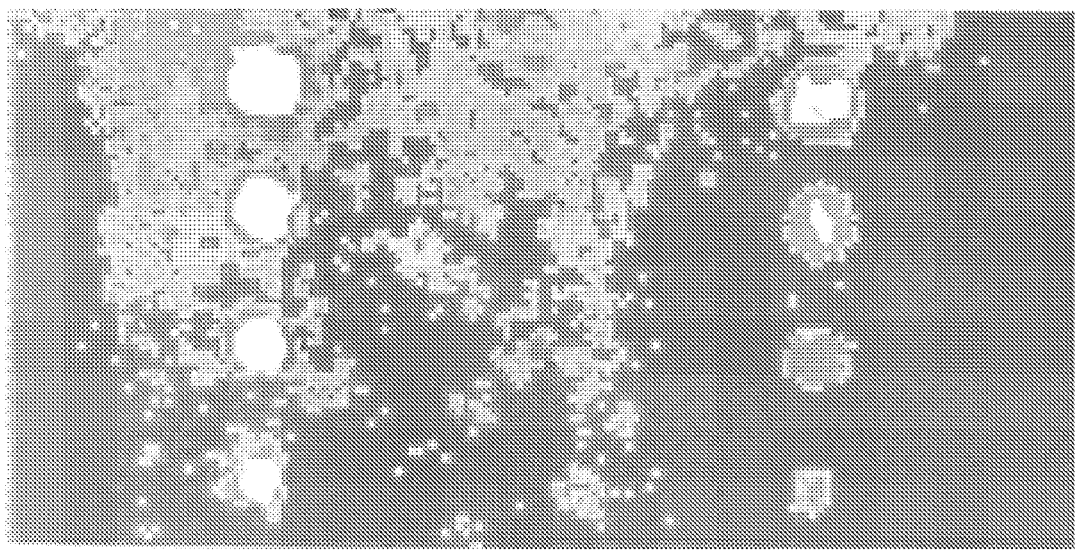
FIG. 4A is an example of ultrasonic mapping.
Figure 4B:
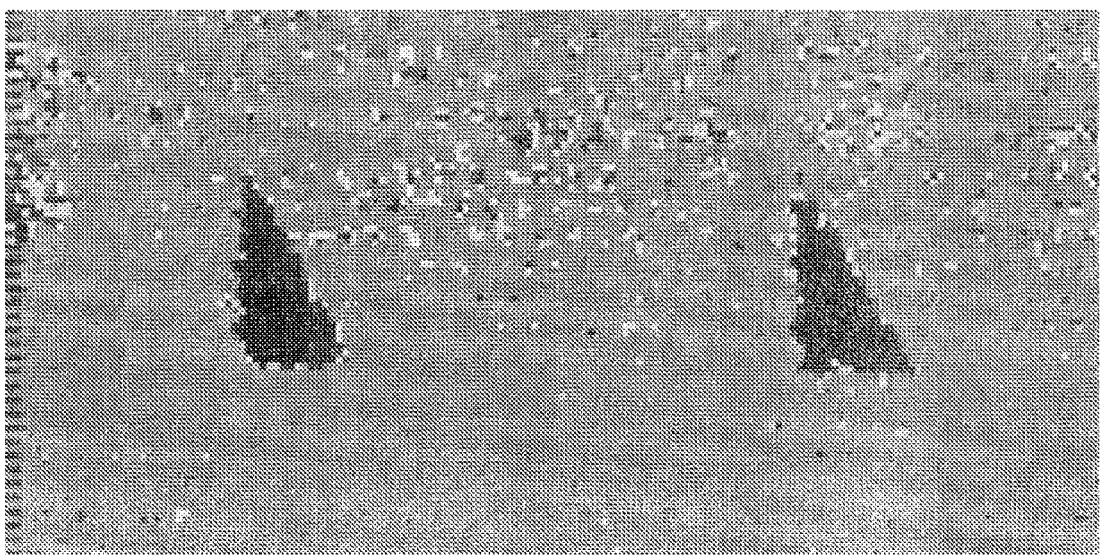
FIG. 4B is another example of ultrasonic mapping.

FIGS. 4B and 5A illustrate ultrasonic signal capture in very attenuative materials such as foam or composite honeycomb (that can be characterized using ultrasonic c-scan approach) and liquid (water) jet probes enabling rapid scanning of the test object.

Depicted in FIG. 4 are ultrasonic signals maps (C-scan presentation) from a bi-static test configuration. The tests are done using custom built, low noise water jets, but can be duplicated using other forms, including air or contact transducers, for medical use. Ultrasonic signals may be time and amplitude gated and processed by electronic frequency filters.

FIG. 4 depicts a graphic picture of the ultrasonic signal changes in a ½ inch foam panel A and 8 in thick honeycomb panel B. This figure illustrates a low frequency scan resolving local signal variances in through transmission test in foam and honeycomb sandwich structure. In an approximately 6 inch high 12 inch wide sample area, local material variances are recorded at sub-wavelength resolution because of transducer and signal processing improvements enhancing possible quality of the data. Figure graphic representation maps data that consist of combined information from a lot of technical factors.

Figure 5:
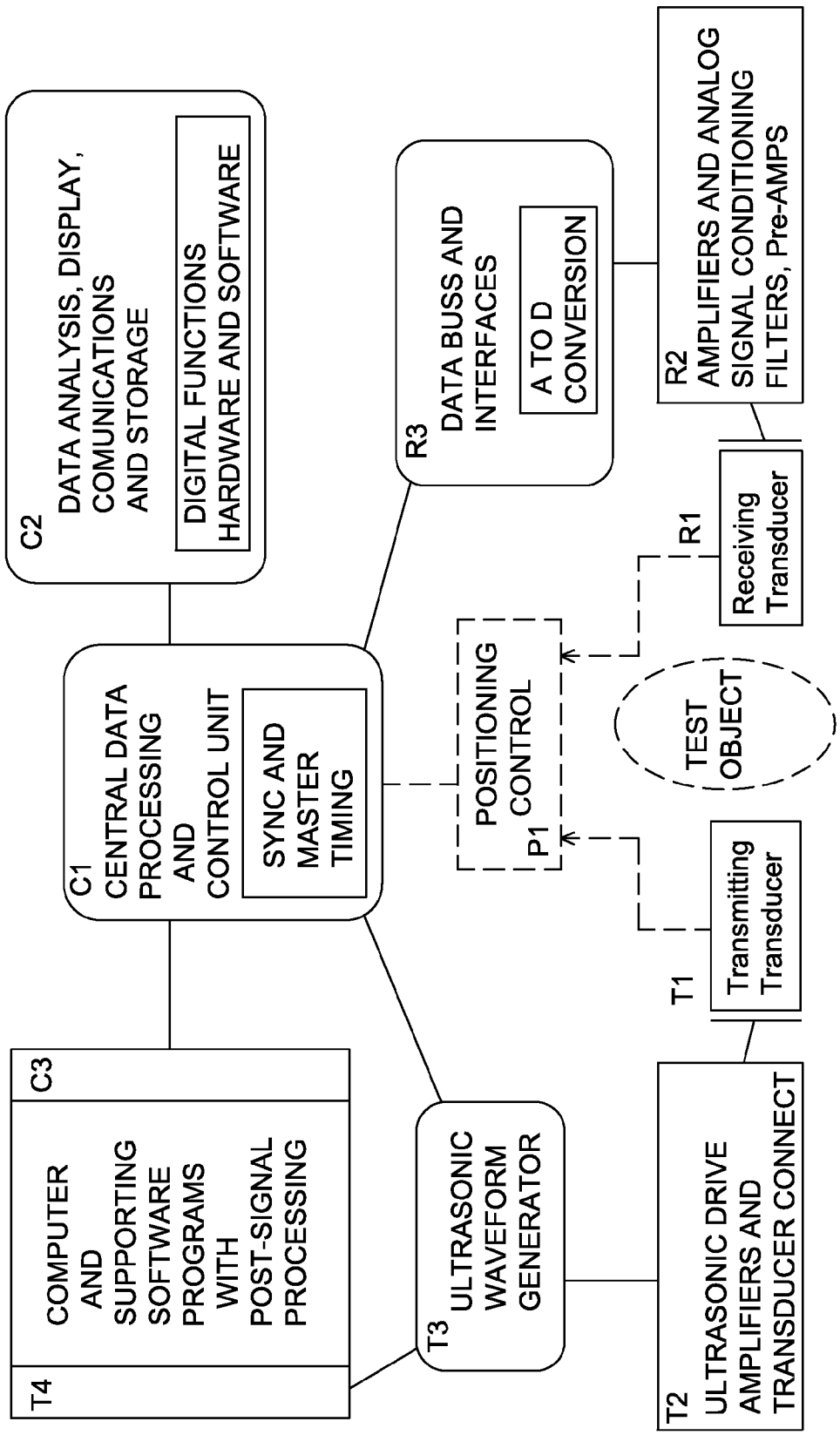
FIG. 5 is a schematic of the working and processing modules of a non-imaging low frequency ultrasound system in accordance with some embodiments herein.

By implementing a gated r.f. drive from about 100 kHz to 1 MHz, controlling the aperture of transducers and working with low noise large dynamic range equipment (pre amplifiers and digitizers), ultrasound can be used in attenuative materials that are conventionally not considered accessible. Aperture of the transducers is governed by the ultrasonic frequency of the tests and the size of the test area. Transmitting transducer must meet aperture size with respect to wavelength considerations described earlier and produce planar wave-front that intensifies the area under the test. Receiving transducers are of sub-wavelength in aperture to resolve fine structure of the ultrasonic wave-front. FIG. 5 illustrates functional components of one embodiment of the advanced ultrasonic diagnostic system. Specific performance characteristics of such a diagnostic system are outlined later in the discussion of the performance requirements. It should be noted that when extracting small signal changes from attenuative biological systems; amplification and the capture with processing of such signal requires very large dynamic range of about 80 to about 120 dB and very low noise front end receiver amplifiers.

FIG. 5 provides a schematic outline of system functions and electronic sub-elements for an exemplary ultrasonic diagnostic system as described herein. FIG. 5 functionally separates the functional components that may be used to create low frequency diagnostic test instruments. When extracting small signal changes from attenuative biological systems; ultrasonic diagnostic instrument signal amplification and the capture with processing of such signal requires very large dynamic range of about 80 dB to about 120 dB and very low noise front end receiver amplifiers. The individual functions can be separated or integrated into a single computer and/or electronic assembly. The transmitting transducer T1 is/are ultrasonic transmitting transducer(s) meeting operation criteria described earlier. Transducers may be an integral part of the mechanical positioning system P1 that enables remote and automated manipulation of the transducer(s). Receiving transducer R1 is/are receiving transducer(s) meeting operation criteria described earlier. Transducers can be an integral part of the mechanical positioning system P1 that enables remote and automated manipulation of the transducer(s). Transmitting transducer T1 may be driven and controlled by ultrasonic drive amplifiers and transducer connect T2 electronic instrumentation that provides electrical signals for excitation of transmitting transducer T1. The frequency and drive signal are provided by ultrasonic waveform generator T3 controlled and interfaced to the central data processing and control unit C1. Central data processing and control unit C1 includes a hardware or software control function that synchronizes operations of the subcomponents and manages traffic of the data and signals to and from other system sub elements. Central data processing and control unit C1 includes data buffers and manages data stream and timing for the full system. Test data is captured via receiving transducer R1 and conditioned by amplifiers and analog signal conditioning filters R2 that include analog functions including pre-amps, amplifiers filters and signal conditioning functions. In one embodiment, the controlled bandwidth of the amplifiers and analog signal conditioning filters R2 is in the range of about 50 KHz to about 5 MHz, with the lowest possible front end noise preferably less than 10 microvolt's into 1 kilo-ohm. In another embodiment, the controlled bandwidth of the amplifiers and analog signal conditioning filters R2 may be in the range of about 20 KHz to about 1 MHz. The amplifiers employ linear response and a desired dynamic range of about 120 dB or greater. Amplifiers and analog signal conditioning filters R2's processed signals are passed to the data bus and interfaces R3 that converts analog data to digital format and supports data bus interface to transfer digital signals to the central data processing and control unit C1. Desired analog to digital conversion, when used, should be better than 14 bit with preferred range at 18 or 20 bits. Data analysis, display communications and storage C2 can be a stand-alone or computer based module that receives digital data from central data processing and control unit C1 and executes rapid analysis, display and storage of the data and processing results information. The computer and support software section C3 of the computer is set as interfaced for external programming, additional post signal processing and all necessary communications with central data processing and control unit C1 and data analysis, display communications and storage C2. Computer and support software T4 section of the computer is dedicated to the support of the ultrasonic transmitting functions including software, programming and external control of the ultrasonic waveform generator T3 and ultrasonic drive amplifiers and transducer connect T2 subsystems.

In an actual system, the key functions identified in the diagram can be shared and/or assigned to other modules depending on the specific operational needs. For example, in a miniaturized and dedicated system set to operate at limited and pre-selected frequencies and data acquisition functions, the central data processing and control unit C1, data analysis, display communications and storage C2, ultrasonic waveform generator T3 and data buss and interfaces R3 can be integrated into a single programmable chip processor. As digital electronic instrumentation changes, it always must be properly interfaced to ultrasonic drive amplifiers and transducer connect T2 and amplifiers and analog signal conditioning filters R2 functions that provide transducer drive and sense transducer received signals. Analog matching of the drive amplifiers to the transmitting transducers and analog sensing of the receiving transducer signal should be of the best quality to meet later digital signal data management.

Medical ultrasound testing is performed in depth using beam forming imaging. In contrast, ultrasonic signal map ping, as shown in FIGS. 4A and 4B, is possible with test set-ups and target cross-sections that are not suitable to medical imaging. The ultrasonic scan can be done in bi-static configurations. Such configurations can identify local density variances, sound path discontinuity or Doppler signals. Signals can be further processed via CT (computerized tomography) algorithms or time of flight algorithms that can create three-dimensional retentions of the test volume.

ducer measures ultrasonic beam changes due to sound transit. No focusing and wavelength dependent imaging is performed.

The table below provides an overall summary of different transduction performance factors. A complex set of criteria and steps, as explained below, is needed to properly acquire ultrasonic data.

| Transducer Probe Type | Distance (Probe to test point) | Sensitivity | Efficiency | Probe Complexity | Scan System Complexity | Signal Fidelity | Body Geometry Practicality |
|---|---|---|---|---|---|---|---|
| Sliding Contact | Contact | High | High | Low | High | Low | Low |
| Immersion | Focal Length | High | Medium | Low | High | High | Medium |
| Bubbler | Contact | High | High | Low | Medium | Medium | Low |
| Water-Jet | 1-20 cm | High | Medium | Medium | Medium | High | High |
| Air | 1-50 cm | Low | Low | Low | Low | Low | High |
| Electro-Magnetic* | <0.2 cm | Low | Low | High | High | Low | Low |
| Laser-Optical | 1-1000+ cm | Medium | Low | High | Medium | High | High |

*Requires electrically conductive material

This work has not been optimized or recognized for medical use, even when these test configurations work at much lower frequencies and sound signal propagates over a broader range of tissue types such as lungs, bone and others. Most tests are possible at frequencies below about 1 MHz. These lower frequencies do not meet wavelength requirements dictated by resolution needs for medical imaging tests.

Shown in FIG. 4A, a zone of the foam panel is examined and c-scan (X-Y plane map) presentation tracks the changes in signal attenuation related to foam material condition. Shades of gray changes represent gated ultrasonic signal intensity. In FIG. 4A lither shades indicate location of mechanical discontinuity defects in the structure while uniform gray background indicates good material. In FIG. 4B the dark triangular indications locate and outline material un-bonded areas at different depth mapped on the one plane presentation. Such mapping can be performed for the body, body parts or specific organs. The ultrasonic test frequencies and transducer set up can be deducted via analysis tools such as illustrated in FIG. 8 and FIG. 9.

Lower frequency ultrasonic testing can be performed with appropriate transduction tools that extend the range of the ultrasonic transducer types. The test applications can include a single transducer or multiple transducers in a linear or non-linear array. Exemplary transducer types include contact transducers, water jet transducers, bubblers, or customized air-coupled transducers. FIG. 6 shows exemplary transducer types available for the lower frequency testing applications. Most medical diagnostic tests are performed via array transducers or a single mechanical scanning transducer often referred to as a wobbler. Either of these arrangements can be used to scan the entire test field.

Figure 7:
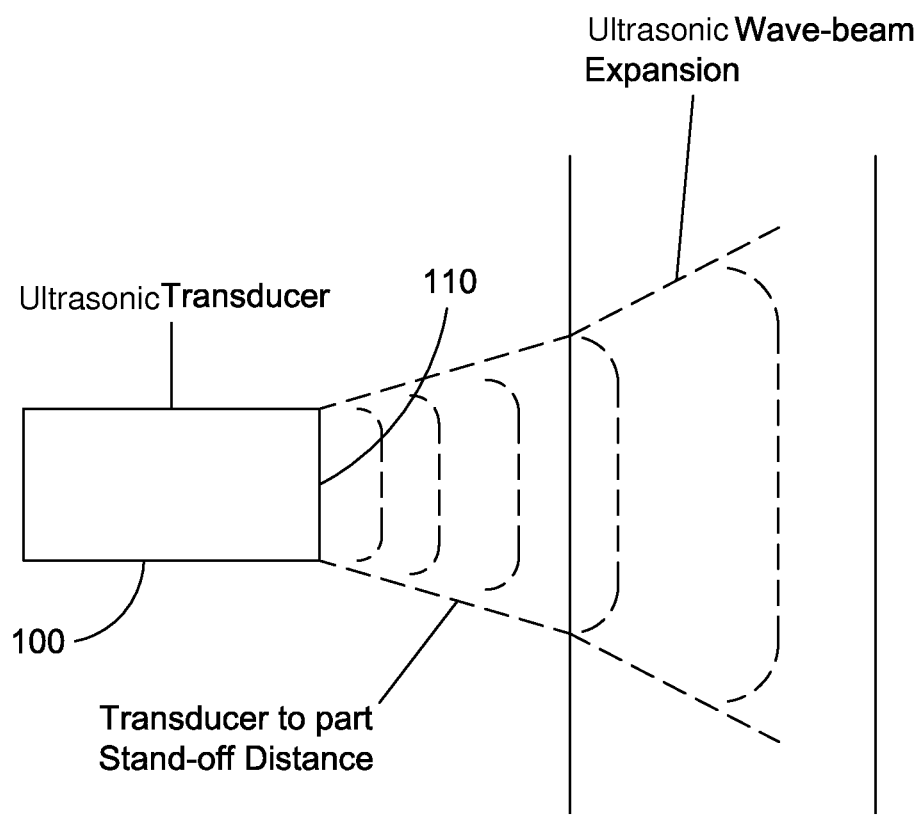
FIG. 7 is an exemplary transmitting transducer suitable for use in some embodiments.

An exemplary transmitting transducer is shown in FIG. 7. The larger aperture source transducer (transmitter) creates a planar acoustical field for low frequency diagnostic testing. Such a transducer can project ultrasonic signals over a large area enabling the ultrasonic signal projection into complex volume areas of the human body. This is a possible source transmitter for the test configurations shown in FIG. 1 to FIG. 3. At these longer wavelengths, the receiving trans- Lower frequency testing extends the range of possible transducers that may be used. Significantly, several types of transducers are suitable for low frequency applications although they may not be suitable for high frequency applications. Suitable transducers for the low frequency applications contemplated herein include contact, transducer arrays, bubbler, water jet, air coupled, waveguide coupled and even most advanced laser ultrasonic configurations. Often, transduction and transducer choice is guided and mandated by cost constraints, test needs and the practicality of the testing configurations. The solution can produce hybrid transducer configurations such as air-coupled generation and contact receivers or water jet transmitter and array receiver and so on. These hybrid configurations enhance the overall system performance by the optimization of the transducer functionality and performance.

Figure 8:
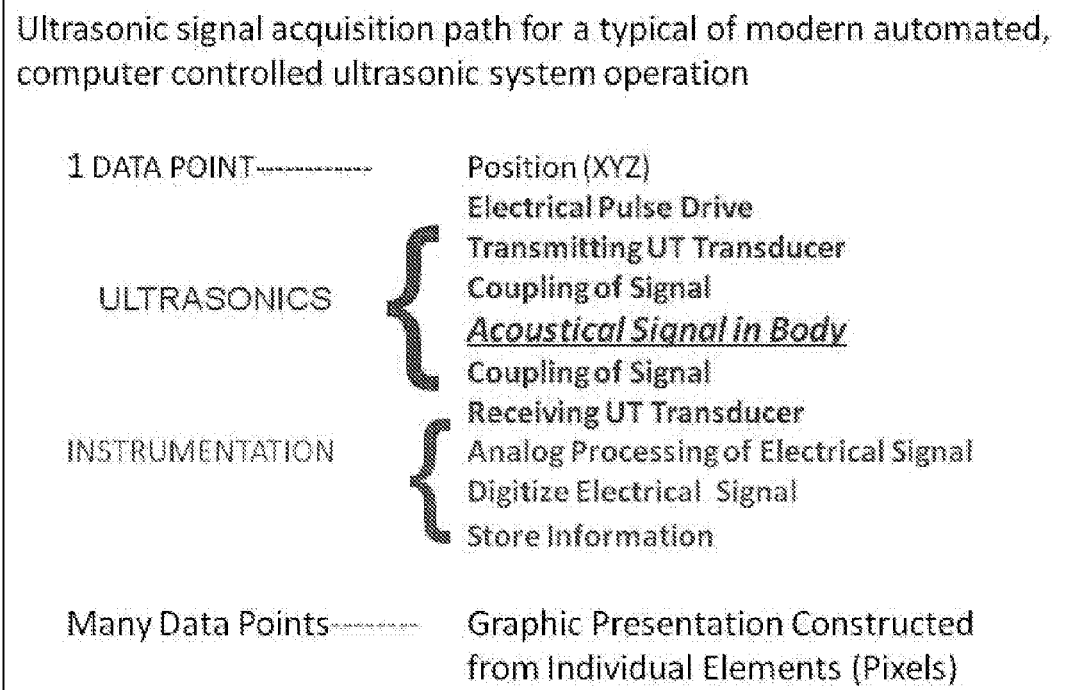
FIG. 8 is a representation of the various steps suitable for ultrasonic signal acquisition in accordance with some embodiments.
Figure 9:
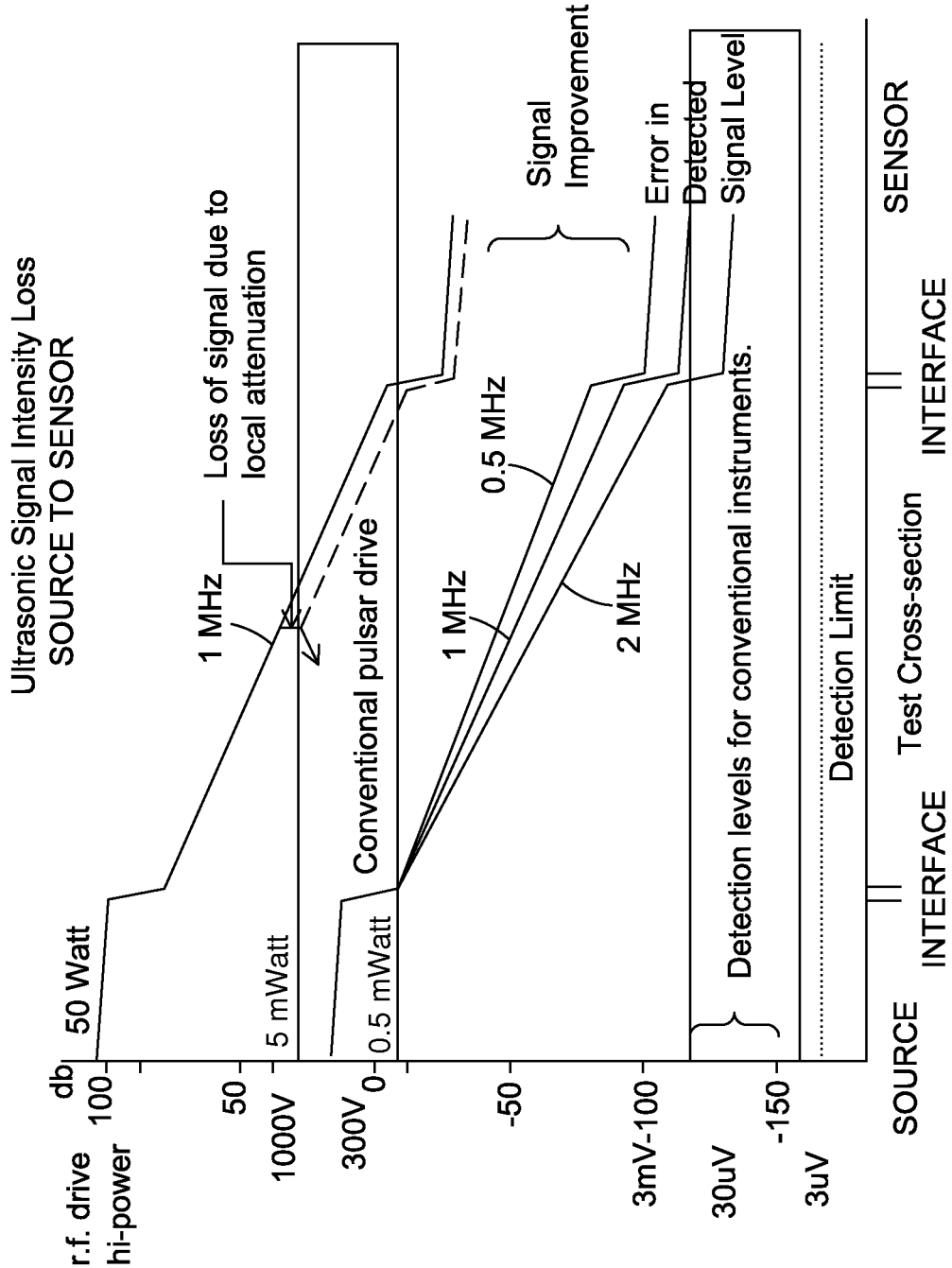
FIG. 9 is a chart depicting ultrasonic signal intensity loss from source to sensor.

Each ultrasonic test measurement creating a data point associated with a specific transducer orientation encompasses a complex process of steps outlined in FIG. 8. Namely, each data point is indicative of a position (XYZ), and is generated from a combination of ultrasonics test parameters including electrical pulse drive, transmitting a low frequency ultrasound, coupling the signal, creating an acoustical signal within the test body, coupling the signal, receiving the signal at a receiving transducer, processing, digitizing and storing the information. The above steps can be augmented via signal processing and signal gating methods, and other techniques. Finally, multiple data points can be assembled into a graphic presentation for ease of understanding.

Combination of multiple data point sets creates input for the mapping of the ultrasonic test data. One ultrasonic test data point includes the ultrasonic signal related information and the instrumentation related capture of this information. The ultrasonic portion of the data is affected by transduction process using transducers as described above that are selectively optimized for the application. The acoustical signal in the body is affected by specific clinical features that are subsequently recognized in the received signals via signal processing procedures that are further discussed and illustrated in FIG. 9, and FIG. 10. Conventional ultrasonic instruments and ultrasonic imaging instrumentation are fundamentally based on the broad band impulse signal sources and capture of the back scattered acoustical signal whose dominant wavelength is shorter or similar to the size of the detectable body features. Imaging resolution is wavelength dependent and thus good image resolution dictates high frequency ultrasonic tests. The medical imaging frequencies are above 1 MHz and most commonly 5 to 15 MHz. The ultrasonic signals at these frequencies are significantly attenuated by many body components (organs), body parts and layered body geometry. In contrast, low frequency planar gated r.f. signals, as used herein, can penetrate most of the body cross-sections and, as illustrated in FIG. 9, enable ultrasonic examination of the body cross-sections inaccessible to higher frequency imaging processes. Clinically significant changes are extracted from the ultrasonic signals via signal processing, utilizing appropriate instrumentation designs as further discussed in FIG. 10.

To reliably apply low frequency ultrasonic tests to clinical applications the data acquisition instrumentation should include one or more of the following:

Appropriate analog amplifiers

Low noise for greater sensitivity (noise figure of less than 10 microvolt's RMS into 1 kilo-ohm)

Linear and large dynamic range of minimum 60 dB to high performance range of about 90 dB to 120 dB.

12 to 14 bit digitizer minimum, preferred 18 to 20 bits, with sampling over about 50 MHz Digital gating and signal amplitude sensing Advanced trigger options including interface trigger functions Extensive data storage functions User friendly interface Signal processing and signal classification tools The above listed and discussed considerations can be graphically summarized in FIG. 9. Sound attenuation through the test path can be tracked and estimated from individual interactions signal losses. As shown in FIG. 9, the frequency, initial source intensity, and path length control the ultrasonic signal level at the receiving transducer. Lower frequency propagates further and attenuation of the sound signal in the path will be transferred and cause signal change at the received signal transducer. In the body and in biological systems, the ultrasonic waves below about 1 MHz can propagate over longer distances that enable complete ultrasonic signal penetration of the body.

As shown in FIG. 9, any signal loss due to local attenuation in the test cross-section is reflected in a signal change at the receiver sensor. The source transducer signal level drastically impacts the ability to receive a valid signal at the sensing transducers. This signal loss diagram demonstrates mapping of the source sound signal to the receiving sensors that records changes in sound intensity due to the test cross-section changes. This figure illustrates the impact of the different frequencies to the applicability of the ultrasonic test. Lowering and controlling source frequency below about 1 MHz drastically improves received signal intensity. The plot additionally demonstrates the consequence of the transmitting transducer drive and transmitting source signal changes. Using narrow band r.f. drive at the transmitting transducer achieves signal level improvements and better signal quality at the receiving transducer thus optimizing the ultrasonic test conditions. Frequencies below about 1 MHz can be realistically propagated in many cross-sections of the body while higher frequencies with shorter wavelength conducive to imaging algorithms processing would not reach the receiver transducer. The above analysis can be extended to many layer body test problem over cross-sections including lungs, head, bones, heart or many others.

To properly interpret ultrasonic signals acquired via diagnostic tests, significant and structured attention should be paid to the process of the signal interpretation. The following discussion concerning signal processing is an expansion of the discussion and process illustrated in FIG. 5 and discussed in text describing that figure.

Figure 10:
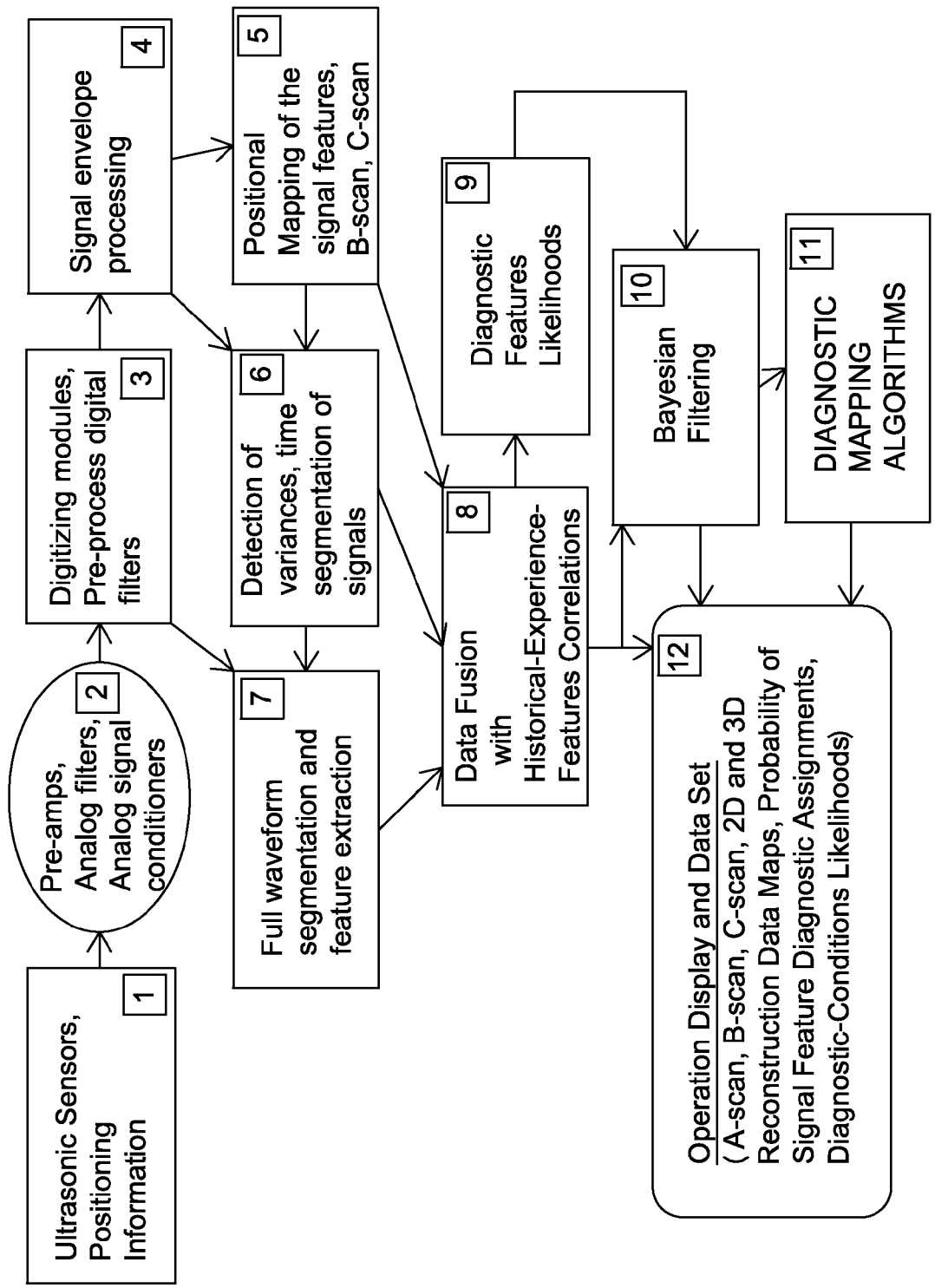
FIG. 10 is a flowchart depicting the signal processing employed by some embodiments.

FIG. 10 is a more detailed schematic outline of the FIG. 5 receiving transducer R1, amplifiers and analog signal conditioning filters R2, data buss and interfaces R3, central data processing and control unit C1 and data analysis, display communications and storage C2 functions specifically focused on the signal processing methodology.

FIG. 10 outlines ultrasonic signal information processing flow and manipulation of the signals to clinically useful "Operator Display and Data Set" in schematic group (12). The signal processing and process flow diagram in FIG. 10 represents information exchange between sub modules and illustrates the decision flow of the ultrasonic signal information. As shown in FIG. 10 the low frequency ultrasonic signal is captured (1), analog amplified (2), digitized (3) and split into two paths. The first path processes envelope signal in Modules (4) and (5). Envelope signal is further processed for the time segmented important signal components (6). Module (3) also provides a second path for a complete r.f. signal to module (7) for feature extraction of the segmented signal according to directions from the module (6). Next, envelope information (5), envelope variance data (6) and r.f. feature extracted data (7) is integrated in a data fusion module (8) and provided to the Operation Display interface (12). Validity of the results is further assessed via module (9) and additional, more advanced processing is possible via additional statistical processing by Bayesian Filtering, module (10) whose results are supported by diagnostic mapping functions in (11) and transferred to the Operation Display (12).

To properly interpret ultrasonic signals acquired via module (1) a structured attention must be paid to the process flow of signal extraction, signal processing and the signal interpretation. Analog signals from the sensing ultrasonic transducer (1) are electronically conditioned in module (2) which delivers analog signals to module (3). In (3) analog signals are appropriately digitized and complete ultrasonic test data is distributed to the envelope processing module (4) that can extract r.f. signal envelope features including shape, positive and negative envelope components, RMS envelope, absolute value envelope, signal energy envelope and similar envelope detection operations. The functionality of the process in (4) is to determine important signal portions of the single ultrasonic signal test data set. Criteria such as signal level above noise, signal energy, signal envelope shape, signal envelope polarity, and similar are used to identify useful segments of the time domain ultrasonic data. This information is transferred to modules (5) that can integrate and map the features of the envelope signals and defines reduced data time segments positions for further processing. Module (5) then provides time and position mapping of the envelope signal information to module (6). Mapping of the envelope signal features can be in many formats including ultrasonic B-scan and C-scan formats. Module (6) identifies important data time segments and fingerprints envelope variances of interest for the module (7). Concurrently module (3) transfers full digital r.f. ultrasonic test data to the module (7) that segments r.f. signals via instructions provided by module (6) analysis of signal envelope features. Module (7) extracts time segmented full r.f. waveform signal and performs related signal features and variances analysis such as amplitude, phase, pulse shape, frequency content, frequency shifts, raise time, arrival times, and/or more complex analytical features. Information from modules (5), (6), and (7) is transferred to and is integrated via "Data Fusion" functions in module (8). Module (8) incorporates historical experience acoustical signatures, clinically significant features information and analytically modeled features. Complete feature correlation and data fusion of information is processed and delivered to the Module (12). When processing strong signal and encountering simpler diagnostic signatures, the data fusion in (8) can be adequate for the diagnostic information in module (12). As fused data is available in (8), it is forwarded to the module (9), to assess Diagnostic Features Likelihoods. For complex ultrasonic tests and in cases when data forwarded from the (8) to (9) is not readily verified by Diagnostics Features Likelihoods module (9) that establishes statistical likelihoods for the recognized signal interpretations and clinical significance, additional data process is triggered. Processed data from module (8) and statistical information elements on the fused data from module (9) are transferred to Bayesian Filtering process module (10). Full (8) and (9) information data undergoes Bayesian Filtering process in module (10) that supports processed signal diagnostic mapping algorithms in modules (11). Complex signal identification via Bayesian inference approach allows a better statistical inference and established statistical likelihoods for the recognized signal interpretations and clinical significance of data by using rigid statistical algorithms, previous signal analysis information, signal features and historical information. Coded information from (10) is transferred to the Module (11) that maps the data interpretation results in formats usable by (12). Integrated information and processed data from (10) and (11) is streamed to the "Operator Display" (12) that functionally supports user interface and graphic display mapping of information of the clinically diagnostic important results.

One or more transducer of the types described above are positioned in testing configurations as outlined, for example, in FIGS. 1 to 3 with knowledge of their positioning (1). Analog signals from the sensing ultrasonic transducer are electronically conditioned via pre-amps, analog filters, impedance matching stages and other appropriate analog signal conditioning electronics that assures integrity and linearity of the signal with dynamic signal to noise ratio in excess of 60 dB with preferred dynamic range of 90 dB to 120 dB depending on the specific application. (2). For example, the more uniform breast tissue simpler diagnostic analysis is possible using 90 dB dynamic signal range while chest cavity or skull cross-section due to the complex nature of the structure would require 120 db dynamic signal amplitude test operations. The analog signals are digitized (3) at significantly large oversample rate at 10 to 1000 times operating frequency range and at better than 12 bit dynamic resolution with preferred 16 bit or better analog to digital conversion when performing advanced signal analysis such as wavelet transforms. Such high fidelity processing assures stability of subsequent signal processing functions. After digitizing module (3), signal is distributed to the envelope processing module (4) that can extract r.f. signal envelope features including shape, positive and negative envelope components, root mean square (RMS) envelope, absolute value envelope, signal energy envelope and similar envelope detection operations. This information is transferred to modules for positional mapping and detection of variances and time segmentation of signals, (5) and (6) that can integrate and map the reduced data positions for further processing. Module (5) provides time and position mapping to module (6) that can identify relevant envelope changes for the module processing. Module (6) further segments data in time sequences of interest for the module (7) analysis that extracts time segmented full r.f. waveform signal related variances such as amplitude, phase or frequency shifts. Information from modules (5), (6), and (7) is integrated via "Data Fusion" functions (8) that incorporate historical experience acoustical signatures, clinically significant features and analytically modeled features. This information is processed in module (9) that establishes statistical likelihoods for the recognized signal interpretations and clinical significance. Modules (8) and (9) feed "Operator Display" (12) and data information interface. Concurrently (8) and (9) information undergoes Filtering process, for example Bayesian filtering, in module (10) that supports a mapping module (11) and a display module (12). Module (11) functionally supports user interface mapping of information of the clinically diagnostic important results weighted by module (10).

It is noted that complex signal identification via Bayesian inference approach allows an improved statistical inference, which is distinct from the more traditional frequentist inference. It is specifically based on the use of Bayesian probabilities that summarizes evidence. The formulation of statistical models for use in Bayesian statistics has the additional feature, not present with other types of statistical techniques that require the formulation of a set of prior distributions for any unknown parameters. Such prior distributions are a significant part of the statistical model and express the combined probability distribution of observations given the model parameters. Set of prior distributions for a recommended findings problem may involve previous experience data, modeled data and ultrasonic signal feature distributions introduced from the specific purpose clinical studies. "Operator Display and Data Set" module (12) enables friendly, customized user interface, information storage, test parameter control interface to FIG. 5 (Computer and support software T4) and (computer and support software section C3) functions and provides graphics and data outputs for the user community.

Examples of some of the medical conditions the present technology will be able to be used for include but are not limited to non-invasive fetal lung development analysis, lung collapse (Pneumothorax) monitoring, lung degradation, chest cavity evaluation, internal bleeding detection, overcoming challenges in transthoracic echocardiography, etc. Other applications in which embodiments of the low frequency ultrasonic testing and diagnostic evaluation system may be used include:

1. For Doppler signals:
   a. characterizing a variety of tissues, such as blood vessels and their blood flow and other related abnormalities and their movements;
   b. heart tissue and their abnormalities and their movement, such as with tissue Doppler mapping;
   c. urine movement, flow, abnormalities;
   d. any other tissues and their related abnormalities and movements; and
   e. any other application in which Doppler may be used.

2. For ultrasound, some embodiments of the invention cover a broad assessment of all the different kinds of tissues such as bone, lung, heart, gastrointestinal, brain, etc., and their abnormalities, masses, structural defects, mechanical defects, presence of foreign object such as projectiles or nails and other related characterizations.

The apparatus and methods described herein can be used to analyze materials whether biological or non-biological in origin. The apparatus and methods are particularly well-suited for use with biological materials, particularly in the medical field for assessment of those biological materials. As such, the apparatus and methods herein are well suited for evaluating medical targets.

Medical targets include any biological tissue, whether live or not, functioning or not may be analyzed. The medical target may include natural and foreign bodies. The biological tissue may be humans, or animal or other origin. Non-biological materials may be in the form of foreign objects, such as bullets, coins, or other items that occasionally find their way into living tissue. Biological tissue includes but is not limited to the entire body, or any part thereof, any body system or part thereof, a combination of body systems or parts thereof, tissues, organs, fluids, including secretions and excretions, bones, cartilage, ligaments and parts or combinations thereof. It should also be clear that any such medical target may also include one or more anomaly, pathology, malfunctioning state, non-functioning state, foreign body (e.g. coin, projectile, obstruction, etc.), space occupying lesion, tumor, scar tissue, etc. that could be analyzed as part of the target.

The analysis may be conducted on any complete or incomplete entity whether living or dead, functioning, non-functioning or malfunctioning. The apparatus and methods may be used to analyze material removed from a living creature. As used herein, an entity can be any of an entire organism, muscle, tissue, organ, or part thereof.

The ultrasound system can analyze any part of the human or other body, any kind of tissue, any cavity, any space, fluid, blood, any foreign body, rupture, laceration, fracture any mass and any pathology, regardless of stage of development: from embryo, fetal, to-neonate (premature if this occurs), infant, toddler, child [pediatric stages], adolescence, adult, and the parallel life stage in non-human entities, as appropriate.

The apparatus and methods described herein can be used to detect functional pathologies/anomalies, detect any anatomical pathologies/anomalies, to characterize material properties and mechanical properties of a targeted pathology, material, or tissue, to measure length, width, volume of any mass or structure (e.g. fetus, hemorrhage, or targeted entity). Mechanical properties can include but not limited to: flexural modulus, young's modulus, thickness, etc. Additional mechanical properties such as, density, ductility, fatigue limit, plasticity, Poisson's ratio, shear modulus, shear strain, specific modulus, specific weight, etc. may also be evaluated with the apparatus and methods described herein. In some instances mechanical properties such as compressive strength, flexural strength, fracture toughness, hardness, shear strength, softness, tensile strength, yield strength, etc. may also be evaluated.

Some embodiments may be developed with specialized capabilities, e.g. Doppler tracking for evaluation of fluid or other movement. For example, with these techniques fluid flow and the vessels carrying fluid may be assessed. Examples of such fluids include but are not limited to blood, urine, lymph, air, spinal fluid, etc. as well as the vessel or tissue that contains them. In this manner, flow obstruction, spasm, or discontinuity can be assessed. Flow obstruction caused by thrombosis or emboli or embolus including pathologies such as but not limited to deep vein thrombosis, superficial vein thrombosis, acute coronary syndromes, dislodgement of plaque in coronary vessel or elsewhere, aneurysm, dissection of vessel, etc.

In other uses, any moving object, internal or external, such as but not limited to muscle including an any malfunction in that movement can be detected. This type of analysis is particularly relevant for evaluation and diagnosis of coronary artery obstruction or spasm, vulnerable plaques in coronary arteries, or other arteries as well as dissections, aneurysms, vasospasms, emboli, thrombosis. Such systems can also be used to assess kinesis of muscle, quantify amplitude, frequency of muscle contraction, measure thickness, density, stiffness, rigidity, flaccidity, compliance, assess for fibrosis, tetany, tissue movement, kinetics, amplitude, discontinuity, and flow gradients. In some embodiments, the apparatus and methods described herein may also be useful in evaluating pressure gradients in and assist in measuring absolute flow and pressure gradients.

One or more of the following systems are generally found in animals and humans and can be subject to testing via the apparatus and methods described herein:

pulmonary including pleura (visceral and parietal pleura), costophrenic recesses, thorax cavity, diaphragm; respiratory (upper respiratory tract (nose, nasopharynx, larynx); and lower respiratory tract (trachea, bronchus, lung); urological; endocrine glands; reproductive (male and female); gastrointestinal system; cardiovascular system including coronary, cardiac, pulmonary, lymphatic, systemic; nervous system; brain; spinal cord; spinal canal; peripheral nervous system; ocular system; musculoskeletal; bone; bone marrow; cartilage; integumentary tissue (including hair, scales, feathers, and nails); urinary; mouth; vocal chords; adipose; breast; and other tissues, organs, and systems.

Analysis of low frequency ultrasonic signatures may be used to identify healthy or unhealthy conditions. In particular, prior known ultrasonic features can be used to recognize and assess whether an abnormal situation exists. Some pathologies that can be tested and diagnosed via the ultrasound apparatus and methods described herein include, but are not limited to stones of salivary glands, tonsil stones, renal calculus, foreign body, benign or malignant tumor, benign or malignant mass, metastasis, abscess, cavitation, multilocular cyst, unilocular cyst, cyst, granuloma, fibrosis, stiffness, hematoma, hemorrhage, fracture, sprain (ligaments), strain (ligaments), mass, edema, space occupying lesion, rupture of organ, inflammation, peritonitis, obstruction of organ or other entity, volvulus of intestines, polyps, ligament tear, slipped entity such as capital femoral epiphysis, stress fractures, osteoporosis, malunion of bone, nonunion of bone, rupture (tendon, uterus, or any other relevant entity), pathologic fracture, osteogenesis imperfecta, rickets, malnutrition, organ failure, hydronephrosis, detrusor instability, muscle spasm, incontinence, vascular spasm, tissue spasm, organ obstruction, flow obstruction caused by thrombosis or emboli or embolus (pathologies can include deep vein thrombosis, superficial vein thrombosis, acute coronary syndromes, dislodgement of plaque in coronary vessel or elsewhere, aneurysm, dissection of vessel, etc.), rupture of vessel, etc.

Examination of the specific body zones is performed by optimized transducer set using guidelines discussed above. Different body sections require different transducers based on the local sound attenuation values and local body geometry. Examples listed below outline exemplary approaches to testing configurations for some typical organs or body sections. For illustration purposes, the examples listed below represent more homogeneous body organs such as a woman's breast, difficult structures such as head, and very complex discontinuous body cross-section such as chest cavity with several organs.

Breast cancer is the most frequently diagnosed cancer in women. X-ray mammography is the current screening convention for breast examination, but it has some significant limitations including potential risk of X-ray ionization radiation. The discomfort of breast compression is also a barrier to some patients, and the imaging of large breasts, dense breasts and small breasts have yielded poor results. To overcome ultrasonic imaging constraints in breast examination an alternate non-imaging, low frequency ultrasonic examination methodology is possible that provides for clinical examination of the full volume of the breast tissue. Although the methodology is adaptable to an extensive set of examination configurations, an exemplary option is described below.

Example

Breast Scan

An examination is performed on a table with prone positioning of the breast surrounded by immersion or water jet ultrasonic coupling transducers. The source transducer is large aperture planar acoustical field as schematically illustrated in FIG. 6 depiction of the source transducer. Multiple receiving transducers are used, in a bi-static mode in both on axis through transmission and angled. Data is collected in bi-static mode as illustrated in FIG. 1 with on axis through transmission scan and in bi-static mode as in FIG. 3 with about 30 degree of axis receiving transducers angle. Data is processed via algorithms sequence outlined in the FIG. 10. Frequency of the r.f. gated impulse test is lowered incrementally to achieve desired dynamic signal-to-noise receiving range of minimum 60 dB. Available examination frequencies are down sequenced starting at 5 MHz, 1 MHz, 750 kHz, 500 kHz and 300 kHz. The frequency test range can be further changed by patient biologics, convenience and the test agreement practices. Data over full volume of the breast is gathered via positioning of the transducer or transducer array. Clinically significant features such as tumors are recognized via dynamic ultrasonic data processing algorithms outlined in the FIG. 10.

Example

Simulated Head Scan

Because the skull is relatively hard and thick, it presents a more complex situation. A head can be examined for the skull or brain conditions using contact, immersion or water jet coupling of transducers. Simple manually positioned contact transducers can be used in a portable diagnostic system. For automated testing with body placed on the back, the head can be placed in horizontal position with back of head placed in a test table opening. Because of the high sound attenuation by a bone (skull), lower frequency testing is conducted at range of 50 kHz to 100 kHz. Applying signal processing outlined in FIG. 10, the bi-statically captured ultrasonic data can be examined for the signs of trauma such as hemorrhages, signs of concussion or physical brain damage.

Example

Simulated Chest Cavity Scan

Because of the number and differences in structures, perhaps the most difficult assessment occurs at the chest cavity. A complex cross section of the chest cavity can be examined using bi-static transducer configurations for signs of collapsed lung, fluid filled lung, internal bleeding, tumors, physical trauma, heart functioning and heart trauma, etc. Because the chest cavity has very attenuative tissues (lungs cells) and open discontinuous spaces, relatively low examination frequencies are used. The range of the most useful test frequencies is estimated at 20 kHz to 50 kHz. These low frequency r.f. gated impulse signals transiting the chest cavity are modified by local organ tissue conditions and thus are capable of capturing clinically relevant organ information.

Figure 11:
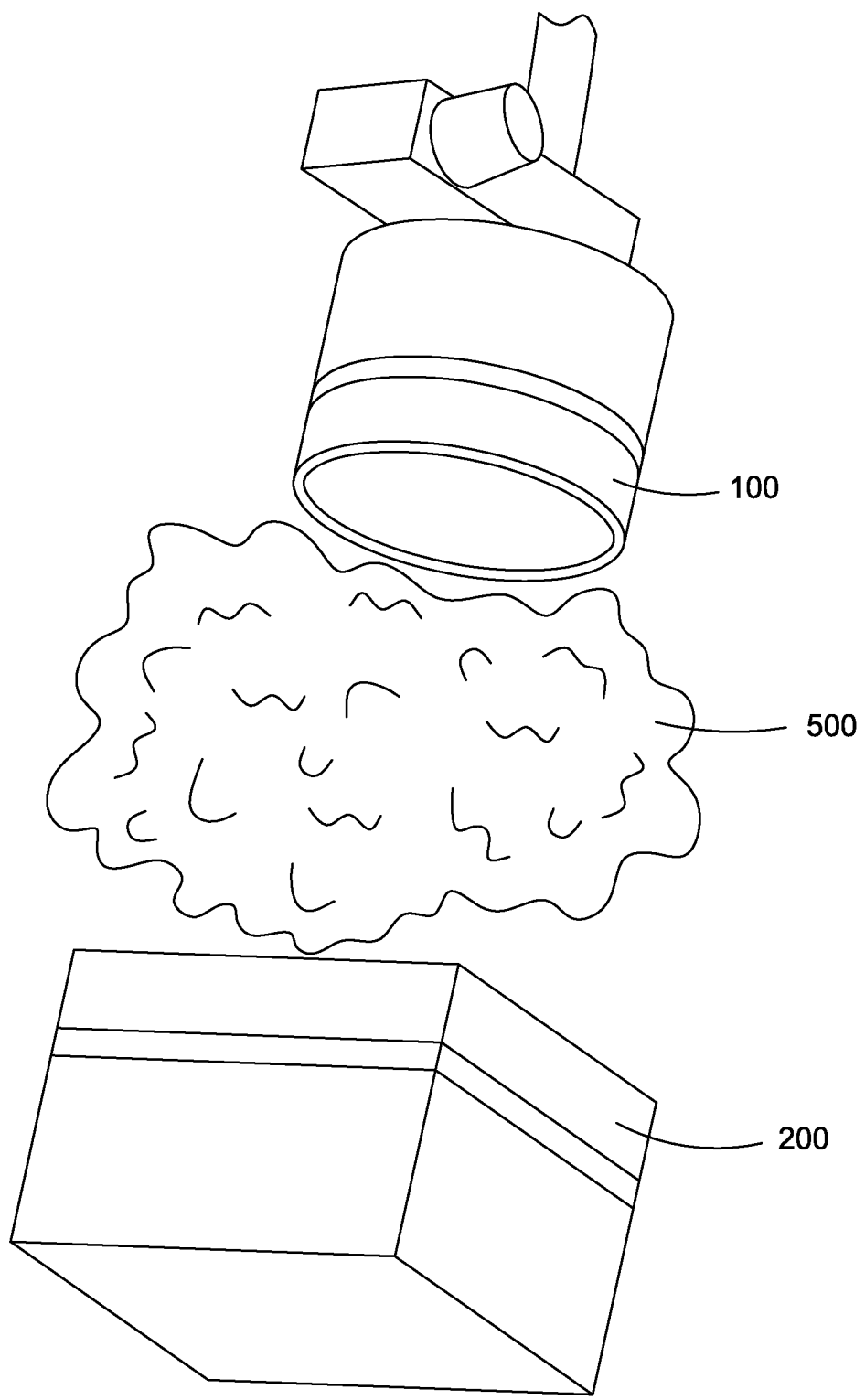
FIG. 11 is a generic rendering of a sample test set up simulating lung tissue.
Figure 12:
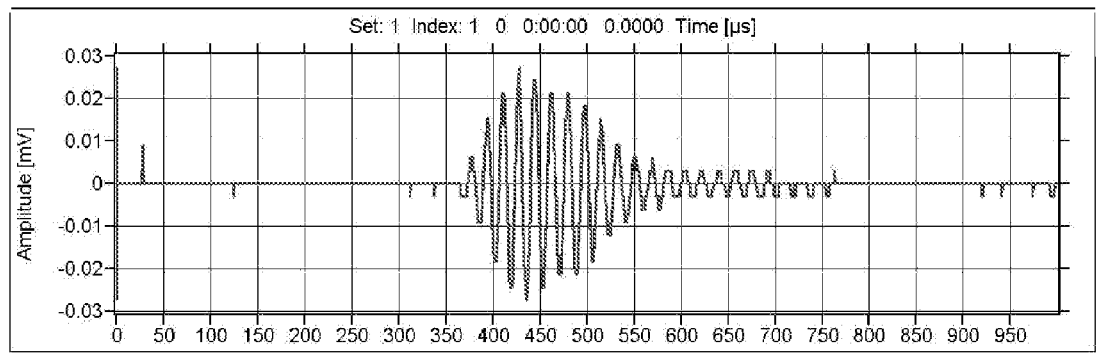
FIG. 12 is captured ultrasonic r.f. signal from air coupled transducers transmitted across about 2 in of lung-like sponge test material.

FIG. 11 is picture of the laboratory test set-up representing ultrasonic evaluation of the lung. This ultrasonic evaluation represents one of the most difficult test conditions using an air coupling non-contact transducer. An air-coupled transmitting transducer 100 is placed opposite an air coupled receiving transducer 200 with the test sample (i.e. sponge) 500 therebetween. Low frequency (64 kHz) ultrasonic test of the acoustical signal transmitted through the wet sponge with soap (e.g. a wet sponge with soap was chosen as an anionic surfactant to model the surfactant component of the lung such as fetal lung). FIG. 12 shows captured ultrasonic r.f. signal from air coupled transducers transmitted across about 2 in of lung like sponge.

Figure 13:
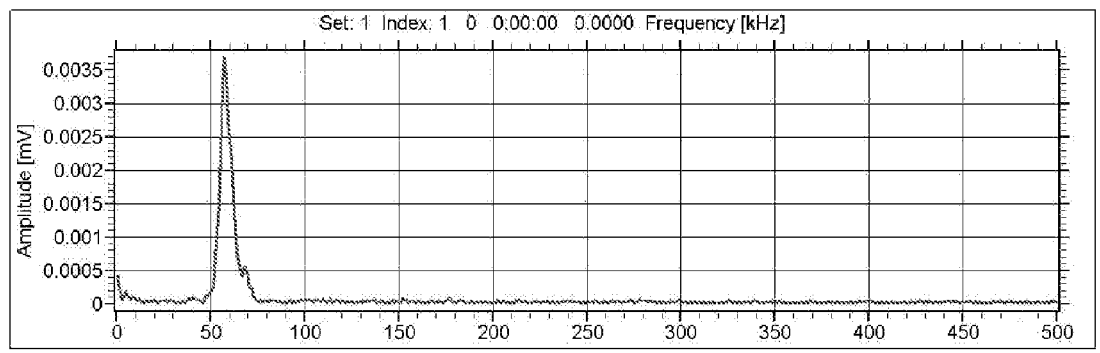
FIG. 13 is a chart of a frequency spectrum of the r.f. signal of FIG. 12.
Figure 14:
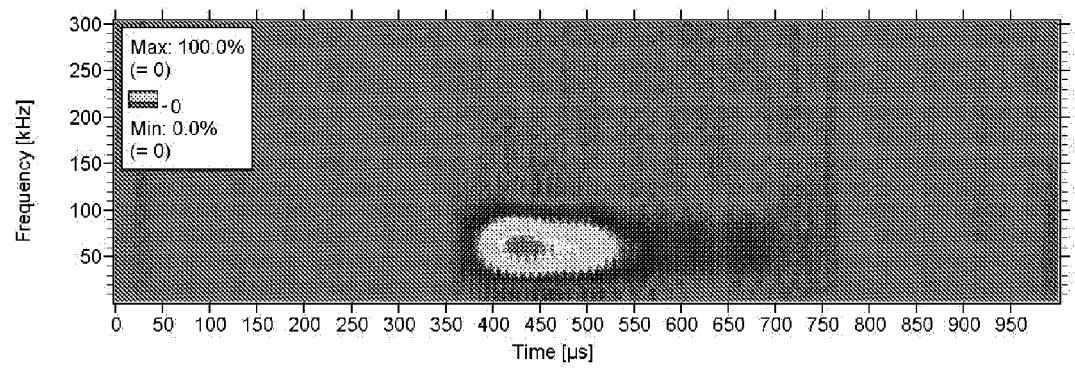
FIG. 14 is a wavelet analysis of the signal depicted in FIG. 12.

FIG. 13 is the frequency spectrum of the r.f. signal in FIG. 12. FIG. 14 is a wavelet analysis of the FIG. 12 signal. The captured and processed ultrasonic signals meet desired characteristics described in the earlier sections and are consistent with the ultrasonic signal quality discussed above. The fidelity of the ultrasonic waveform enables future detailed analysis of the ultrasonic signal changes due to possible tissue degradation in the lungs. The r.f. impulse ultrasonic signals source enable very detailed structured analysis of the signal changes with respect to signal frequency, signal phase, signal attenuation and nonlinear acoustic changes due to the signal scattering, frequency dependent attenuation and signal mode changes due to the body geometry features. Transient ultrasonic examination signal can be resonantly modified by body geometry features including presence of tumors and growth, can be attenuated by human tissue cell changes, can be frequency modulated by dynamic motions of fluids or spasms. Such ultrasonic signal detail changes can be cataloged to the specific clinical conditions and clinically significant medical conditions.

Figure 15:
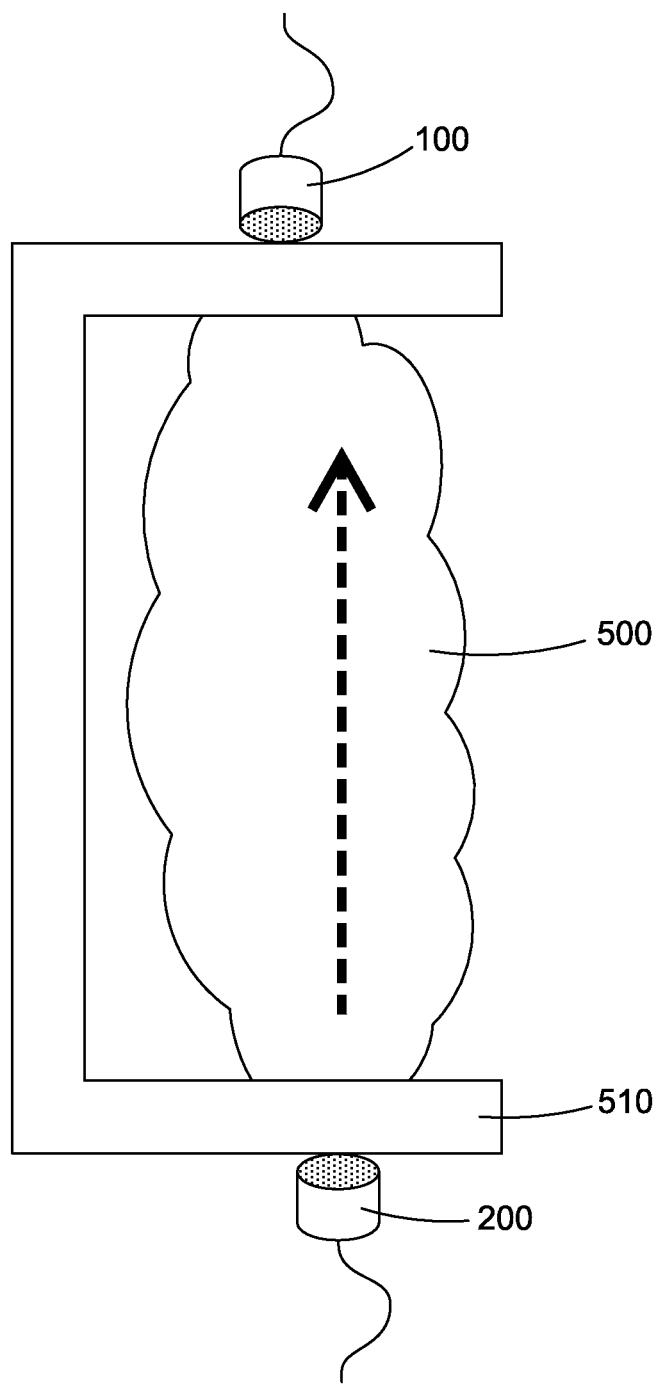
FIG. 15 is a generic rendering of an alternative test set up simulating the chest cavity.

More complex ultrasonic signals are captured in the chest-cavity analog test-phantom as shown in FIG. 15. FIG. 15 depicts the schematic of the chest test phantom cavity cross-section outline. This simulated configuration was constructed from plastic wall containers demonstrating significantly better ultrasonic penetrating power of the r.f impulse low frequency ultrasonic waves. As illustrated, the test configuration cannot support the conventional ultrasonic medical test methods. Low frequency r.f. ultrasonic signals were demonstrated to propagate across this very complex and attenuative path geometry configuration that includes, walls 510, gelatin, sponge 500 and air gaps. Digitally captured and analyzed ultrasonic signals shown in FIG. 16 are representative of the signal differences for empty cavity and signals in the cavity with the sponge.

Gelatin walls included wood lattice emulating a chest cavity rib structure. The low frequency ultrasound signals propagate as guided waves in the gelatin walls, with early arrival times at the sensing transducer and at a slower air dominated direct path through the sponge. FIG. 16 shows amplitude ultrasonic signals, frequency spectrum and wavelet deconvolution of the different ultrasonic signals signatures. As shown in FIG. 15, custom transducers at low frequencies enable signal capture across the cavity including gelatin walls (1.5 cm) and sponge cavity (20 cm).

Figure 16:
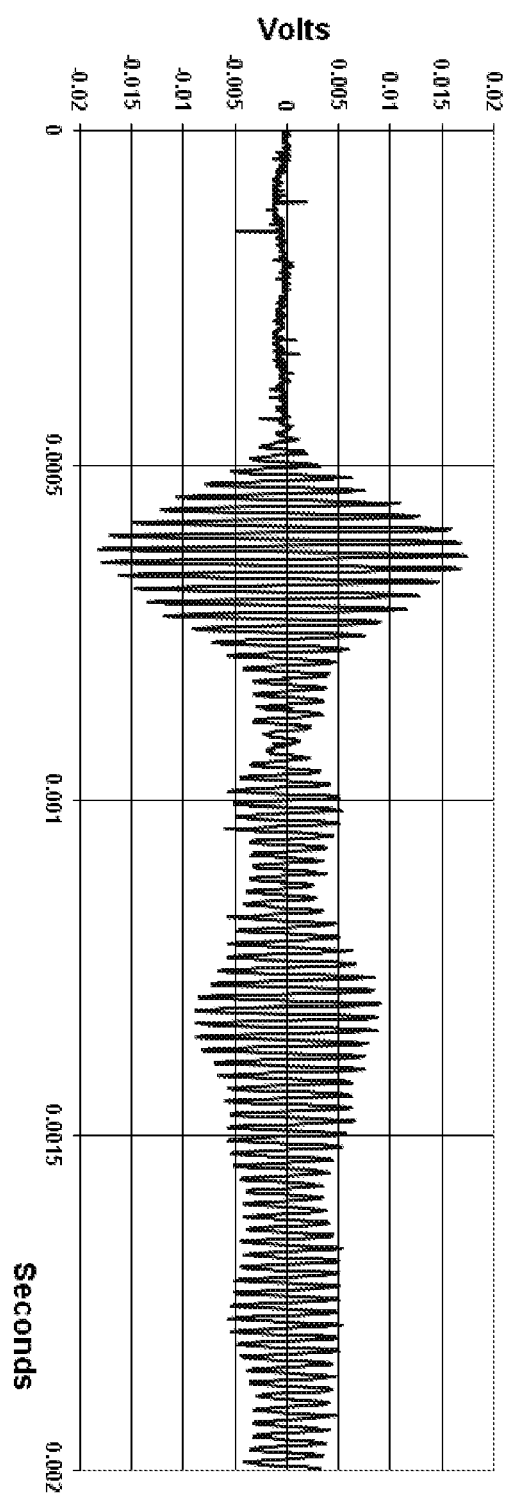
FIG. 16 is captured ultrasonic r.f. signal from another exemplary set up.
Figure 17:
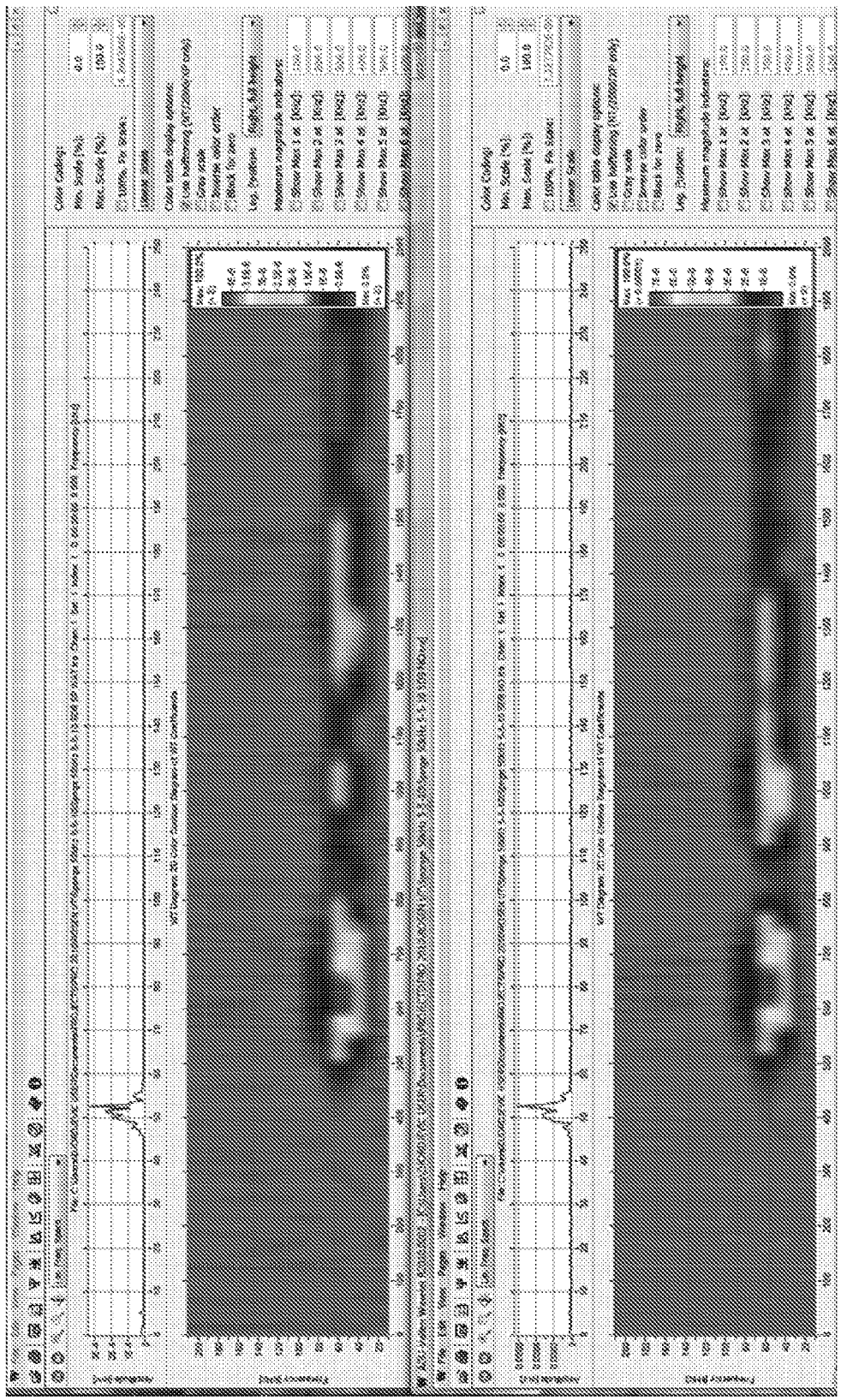
FIG. 17 is a screen shot showing both the spectral readout and the waveform of normal and abnormal lung tissue.

Signals, such as shown in FIG. 16 are complex and are to be processed via signal processing protocol illustrated in FIG. 10. A partial example of signal characterization is illustrated by signal features visible in the wavelet analysis of the r.f. waveforms in FIG. 16. Captured ultrasonic signal transiting a cavity from FIG. 15 is processed with a wavelet analysis tool and is mapped as a frequency, time and intensity plot and shown in FIG. 17. Two maps depicting normal lung, top image, and collapsed lung condition, bottom image are shown in FIG. 17. Bottom wavelet map shows missing signal time gap and changed signal frequency content characteristics following the primary transit wave.

The test set up demonstrates the feasibility to propagate ultrasonic signal in biological media and in body cavity configurations that are traditionally considered inaccessible for the ultrasonic evaluation. The low frequency ultrasonic signals interact and are modulated by the local media conditions and further analysis of the signal makes possible diagnostic identification of the conditions in the examination area. This non-imaging process requires signal processing akin to sonar work and depends on analytical signal target feature extraction from the ultrasonic r.f. signals. Modern computers, digitizing technology and mathematical analysis tools make this approach extendable to the automated diagnostics of the ultrasonic signal response. Features of modern signal processing tools, data acquisition technology and ultrasonic transduction knowledge at the low frequencies, 30 to 1000 kHz has not been technically explored for the medical applications, until now. Based on simple experimental analog test article evaluation, it was possible with non-optimized transducers and test equipment to acquire ultrasonic signals in configurations that, absent the apparatus and methods disclosed herein, would not permit the capture of any signal even using best current medical ultrasonic instrumentation. Exploration of the low frequency sound interactions in search of clinically significant conditions enable a whole new area of ultrasound diagnostic applications that can access a larger volume of the body.

In some embodiments, the apparatus and methods project r.f. gated impulses of low frequency ultrasonic planar wavefronts into the test object, such as the body, body zones and body parts. The gated frequency source frequency content can be controlled via length and shaping of the impulse envelope. The frequency content and r.f. wave impulse characteristics can be controlled via frequency shift within the r.f. impulse signal. Typical example is an up or down frequency chirp r.f. source. The gated r.f impulse comprises two or more selected low frequency wavelength components representing wavelength cycle oscillations in the body tissue mass. Gated electronic frequency source and ultrasonic generating transducers can be matched to produce acoustical signals with specific r.f. impulse characteristic in a low frequency ultrasonic wave domain. The bandwidth of the ultrasonic r.f. source can be controlled so as to minimize effects of the attenuation dispersion of the sound propagation in the body. The projected ultrasonic r.f. gated impulse can be a non-focused continuous planar wave at the source. In some embodiments, the simplest form of the r.f. impulse signal is single frequency two to five wavelengths impulse ultrasonic planar wave generated normal to the large aperture ultrasonic transducer.

In some embodiments, the apparatus and methods project r.f. gated impulses of low frequency ultrasonic planar wavefronts into the test object such as the body, body zones and body parts. The source transducer has a large non-focusing aperture with minimum dimension of about five acoustical test wavelengths at the test frequencies. The source transducer (transmitting transducer) can be a large aperture, low frequency immersion piezoelectric transducer, a low frequency adapted, water jet device coupling ultrasound to the body, a low frequency, air coupled transducer coupling ultrasound to the body.

In some embodiments, the receiving transducer configuration is bi-static or mono-static configuration with a subwavelength receiving apertures, and can be directionally oriented to the best signal acquisition positions. The capture signal can have linear response with useful dynamic range to be better than about 60 to 80 dB. The receiving transducer effective test aperture size dimension can be less than a thirty percent of the ultrasonic test wavelength. Signal capture can be on the normal axis of the source transducer orientation at several locations by moving the receiving transducer or via an array of receiving transducers. Ultrasonic signal capture off-normal axis due to ultrasonic scattering, ultrasonic reflected or refracted waves can also be captured. The receiving transducer can be selected from the same types of transducers as the transmitting transducer, and may be the same type or different type than the transmitting transducer. High fidelity ultrasonic signal capture (sensing) that has been modified by body and clinically significant features can cause one or more of frequency change, ultrasonic wavefront distortions, signal attenuation, signal scattering and/or other feature changes to the original ultrasonic source signals which can be detected and analyzed. In some embodiments, continuous tracking and accurate orientation information can be used on the ultrasonic source and receiver position and orientation including constant reference to the source signals quality to aid in the signal processing and analysis. Data analysis can be performed consistent with information on the location and performance of the transmitting and receiving transducers to enable mapping as stipulated by signal processing operations. In some embodiments, controlled positioning and ultrasonic test parameters with test data intervals can be established to acquire a working data set necessary for the diagnostic mapping output.

Although the examples and disclosure above were written with respect to some specific examples, the breast, the head, and the chest cavity, the disclosure here is not limited to such areas. Indeed, as discussed earlier, the low frequency non-imaging ultrasonic apparatus and methods described herein are useful in a variety of areas. The examples and description herein is meant to be exemplary only.

What is claimed is:

1. A method employing low frequency ultrasonics for medical diagnosis, the method comprising:
   projecting planar r.f. gated low frequency ultrasonic signal into a test object using one or more transmitting transducers, each transmitting transducer comprising an aperture, each transmitting transducer aperture having a width about 2 to about 100 times the acoustical wavelength of each low frequency ultrasonic signal, wherein the low frequency is a frequency from about 20 kHz to about 1 MHz, wherein each of the projected low frequency ultrasonic signals in the test object is affected and modified by internal features of the test object thereby generating one or more reflected, refracted, scattered or transmitted low frequency ultrasonic signals;
   concurrently receiving the one or more reflected, refracted, scattered or transmitted low frequency ultrasonic signals from the test object using a mechanical scanning receiving transducer, having an aperture or two or more receiving transducers, each having an aperture or a receiving transducer array comprising a plurality of receiving transducers with different apertures, each receiving transducer aperture having a width of about 0.01 to about 0.9 times the acoustical wavelength of each projected low frequency ultrasonic signal, wherein the received ultrasonic signals represent the acoustically different internal features of the test object;

receiving the received ultrasonic signals using large dynamic range instruments having a signal to noise ratio of at least 60 dB;

processing the received ultrasonic signals to extract changes in the received ultrasonic signals compared to the projected low frequency ultrasonic signals; and correlating the processed signals, using a processor, to medically significant features of the test object for medical diagnosis.

2. The method of claim 1, wherein the receiving of the received ultrasonic signals is performed by a broadband immersion piezoelectric sensor with sub-wavelength receiving aperture or a water jet probe with sub-wavelength receiving aperture and further comprises conditioning the signals by one or more high dynamic range amplifiers and one or more analog signal conditioning filters.

3. The method of claim 2, wherein a controlled bandwidth of the one or more amplifiers and one or more analog signal conditioning filters is in the range of about 20 kHz to about 1 MHz.

4. The method of claim 2, wherein processing the received ultrasonic signals further comprises time domain ultrasonic signal gating and segmenting to select and separate predetermined ultrasonic signal slices as determined by dynamic signal capture processing.

5. The method of claim 2, wherein the received low frequency ultrasonic signals are captured as r.f. acoustical amplitude signals and envelope signals suitable for digital signal processing, wherein the signal processing further comprises:

processing data records of the r.f. acoustical amplitude signals to define clinically significant portions of the data;

processing the envelope signals to define clinically relevant signatures;

time segmenting the r.f. acoustical amplitude signals to components determined by envelope analysis;

analyzing the r.f. acoustical amplitude signals for clinically significant features; and fusing data from the r.f. acoustical amplitude signals and the envelope signals processing and performing statistical analysis using historical data and clinically significant ultrasonic feature markers to predict clinical diagnosis.

6. The method of claim 5, wherein the statistical analysis is a Bayesian type statistical analysis.

7. The method of claim 1, wherein the correlating the processed signals further comprises data point sets mapping the processed signals to clinically significant information relating to the test object.

8. The method of claim 1, wherein the presence of a medical condition is extracted from a comparison of observed changes in the received ultrasonic signals to historical data.

9. The method of claim 1, wherein the processed signals comprise a plurality of data points relating to the test object, wherein grouping of data points is indicative of a possible target of medical significance and position within the test object, wherein the method further comprises mapping the plurality of data points in a graphical representation to help with medical diagnosis.

10. A non-imaging low frequency ultrasonic evaluation system, the system comprising:

a transmitting transducer for transmitting a planar r.f gated low frequency wavefront of a test frequency from 20 kHz to 1 MHz that defines test wavelength, wherein the transmitting transducer comprises an aperture that has a width that is 2-100 times the test wavelength;

a mechanical scanning receiving transducer, two or more receiving transducers or an array of receiving transducers, wherein each receiving transducer comprises an aperture that has a width that is a fraction of the test wavelength;

large dynamic range instruments having a signal to noise ratio of at least 60 dB;

an analog signal processor and digitizer; and a microprocessor adapted to receive, store and display data obtained via the receiving transducer.

11. The system of claim 10, wherein the transmitting transducer and each receiving transducer is independently selected from no contact air-coupled transducers, water jet transducers, contact transducers, immersion piezoelectric transducers, laser ultrasonic transducers and combinations thereof.

12. The system of claim 11, wherein the transmitting transducer and the receiving transducer are of different types.

13. The system of claim 10, wherein the transmitting transducer aperture has a width of about 5 times the test wavelength.

14. The system of claim 10, wherein the receiving transducer comprises an aperture that has a width that is less than about 30% of the test wavelength.

15. The system of claim 10, wherein the receiving transducer comprises a plurality of receiving transducers.

16. The system of claim 10, wherein the receiving transducer is configured as a bi-static system.

17. The system of claim 10, wherein the receiving transducer is configured as a mono-static system.

18. A method of evaluating a test object via non-imaging low frequency ultrasound, the method comprising:

projecting a planar r.f. gated low frequency ultrasonic wavefront having a test frequency of 20 kHz to 1 MHz that defines test wavelengths into a test object via a transmitting ultrasonic transducer; and receiving, via a mechanical scanning, receiving transducer, two or more receiving transducers having a mono-static or bi-static configuration or an array of receiving ultrasonic transducers, having a mono-static or bi-static configuration, ultrasonic signals that have been modified from the projected ultrasonic wavefront by one or more significant acoustical features of the test object that cause one or more of frequency change, ultrasonic wavefront distortion, signal attenuation, signal scattering, arrival time delay or other change to the projected planar r.f gated ultrasonic wavefront;

capturing the received ultrasonic signals using large dynamic range instruments having a signal to noise ratio of at least 60 dB;

processing the received ultrasonic signals to extract changes in the received ultrasonic signals compared to the projected wavefront and to acquire spatial and time domain information; and using a processor, correlating the extracted changes in the processed signals to medically significant features of the test object for medical diagnosis;

performing data analysis on the changes in the received ultrasonic signals to enable spatial and time domain mapping of medically significant features as a graphical representation of the results of data analysis.

19. The method of claim 18, wherein the projected planar r.f gated ultrasonic wavefront is a single frequency, 2-5 wavelength impulse ultrasonic planar wave generated normal to the transmitting ultrasonic transducer.

20. The method of claim 18, wherein the projected planar r.f gated low frequency ultrasonic wavefront has a center frequency of less than 1 MHz.

21. The method of claim 18, wherein the projected planar r.f gated low frequency ultrasonic wavefront is at a controlled and selected frequency resulting in an ultrasonic waveform of about two to five wavelengths.

22. The method of claim 18, wherein the projected planar r.f gated ultrasonic wavefront comprises r.f gated planar impulses.

23. The method of claim 22, wherein the r.f. gated planar wavefront impulses comprise two or more low frequency wavelengths.

24. The method of claim 18, wherein the projected planar r.f gated ultrasonic wavefront is a non-focused wavefront for examination of breast tissue.

25. The method of claim 24, wherein the wavefront is generated by an immersion or water jet transmitting transducer comprising an aperture that has a width that is a 2-100 times one of the test wavelengths at the test frequency.

26. The method of claim 24, wherein the modified ultrasonic signals are received by one or more immersion or water jet receiving transducers comprising an aperture that has a width that is a fraction of the length of one of the test wavelengths at the test frequency.

27. The method of claim 18, wherein the test object is selected from a living organism, a dead organism, living tissue, non-living tissue, functioning tissue, malfunctioning tissue, or non-functioning tissue, and combinations thereof.

28. The method of claim 18, wherein the test object is a human body part selected from the head, the chest cavity, and the breast.

29. The method of claim 18, where the test object is a human body system.

* * * * *